United States Patent [19]

Heifetz et al.

[11] Patent Number: 4,929,706
[45] Date of Patent: May 29, 1990

[54] CELL GROWTH ENHANCERS AND/OR ANTIBODY PRODUCTION STIMULATORS COMPRISING CHEMICALLY MODIFIED HYDROPHILIC POLYUREA-URETHANE PREPOLYMERS AND POLYMERS

[75] Inventors: Aaron H. Heifetz, Columbia, Md.; Richard A. Wolfe, Ellisville, Mo.; James A. Braatz, Beltsville; Narender P. Luthra, Columbia, both of Md.

[73] Assignee: W. R. Grace & Co.-Conn., New York, N.Y.

[21] Appl. No.: 319,458

[22] Filed: Mar. 3, 1989

Related U.S. Application Data

[63] Continuation-in-part of Ser. No. 266,445, Nov. 2, 1988.

[51] Int. Cl.$^5$ .............................................. C08G 18/10
[52] U.S. Cl. .................................... 528/49; 528/60; 528/66
[58] Field of Search ............................ 528/49, 60, 66

[56] References Cited

U.S. PATENT DOCUMENTS

| | | | |
|---|---|---|---|
| 3,939,123 | 2/1980 | Matthews | 260/77.5 |
| 4,177,038 | 12/1979 | Biebricher et al. | 528/60 |
| 4,182,827 | 1/1980 | Jones | 528/60 |
| 4,226,935 | 10/1980 | Fusee | 528/60 |
| 4,241,537 | 12/1980 | Wood | 47/77 |
| 4,439,585 | 3/1984 | Gould et al. | 525/127 |
| 4,485,227 | 11/1984 | Fox | 528/67 |
| 4,569,981 | 3/1986 | Wenzel et al. | 528/67 |

FOREIGN PATENT DOCUMENTS 248656 2/1988 European Pat. Off. .
87/00248 8/1987 World Int. Prop. O. .

OTHER PUBLICATIONS

Mizrahi, "Primatone RL in Mammalian Cell Culture Media"; Biotechnology and Bioengineering, vol. 19, pp. 1557-1561, (1977).

Mizrahi, "Pluronic Polyols in Human Lymphocyte Cell Line Cultures,"; Journal of Clinical Microbiology, vol. 2, pp. 22-13, (Jul. 1975).

"Pluronic Polyols in Cosmetics"; a brochure published by Wyandotte Chemicals Corporation, 1979.

Article—"Scale-up of Insect Cell Cultures: Protective Effects of Pluronic F-68" Biotechnology, vol. 6, pp. 1411-18.

Schacter, "Serum Free Medium for Growth Factor Dependent and—Independent Plasma Cytomas and Hybridomas"; Journal of Immunological Methods, vol. 99, pp. 259-270, (1987).

Velez et al, "Kinetics of Monoclonal Antibody Production in Low Serum Growth Medium"; Journal of Immunological Methods, vol. 86, pp. 45-52, (1986).

*Primary Examiner*—Maurice J. Welsh
*Attorney, Agent, or Firm*—Charles A. Cross

[57] ABSTRACT

Modified hydrophilic prepolymers and polymers are disclosed wherein the prepolymers and polymers are characterized by cell growth enhancement, and, in some instances, antibody production stimulation. Isocyanate-capped oxyethylene-based prepolymers are modified by reaction with a compound having at least one isocyanate (NCO) reactive group. Preferably, the NCO reactive group is a sulfhydryl group, an amino group or a carboxyl group, in quantities sufficient to modify at least a portion of the isocyanate groups of the prepolymer. The prepolymer and polymer also express a free functional group, preferably an amino, sulfonic acid or a sulfhydryl. When the free functional group is sulfhydryl or sulfonic acid, antibody production stimulation, as well as cell growth enhancement, is observed.

60 Claims, No Drawings

CELL GROWTH ENHANCERS AND/OR ANTIBODY PRODUCTION STIMULATORS COMPRISING CHEMICALLY MODIFIED HYDROPHILIC POLYUREA-URETHANE PREPOLYMERS AND POLYMERS

This application is a continuation-in-part of Ser. No. 266,445 filed Nov. 2, 1988.

BACKGROUND OF THE INVENTION

This invention relates to additives in growth media used for cultured cell lines. In particular, the invention relates to mammalian cell growth enhancers and antibody production stimulators comprising a unique series of modified or derivatized prepolymers and polymers. The prepolymers are formed from isocyanate end-capped monomers and polyols which are substantially ethylene oxide based units. Modification is accomplished by contacting the prepolymer with a reactive compound having at least one NCO-reactive group. NCO-reactivity can be found in sulfhydryl (—SH), amine (—NH$_2$), or carboxyl (—COOH) groups. Upon modification of the NCO groups, the derivative compounds express an additional "free" functional group and are characterized by cell growth enhancement properties. This is particularly so when the free functional group on the modified prepolymer or polymer is either a sulfhydryl, (—SH), a sulfonic acid group (SO$_2$OH) or a free amino (—NH$_2$) In some instances, e.g. when a sulfhydryl or sulfonic acid is expressed, cellular antibody production is stimulated. Further, a modified prepolymer or polymer may express two or more of the above functional groups. The final form of the claimed cell growth enhancer and/or antibody production stimulator can be in the form of modified prepolymer, modified polymeric units from polymerization of the modified prepolymer or modified polymeric units comprising the dissolution product from polyurethane gels formed from the modified prepolymer.

A. Prior Art Prepolymers and Resulting Hydrogels

Numerous polyurethane polymers both foamed and nonfoamed, have been previously identified. Of the nonfoamed materials, quite a few hydrogel polymers, prepared from various prepolymers have been prepared and used for widely varying applications. Typically, hydrogels are formed by polymerizing a hydrophilic monomer in an aqueous solution under conditions such that the prepolymer becomes crosslinked, forming a three-dimensional polymeric network which gels the solution. Polyurethane hydrogels are formed by polymerization of isocyanate-end capped prepolymers to create urea and urethane linkages.

Representative examples of previously disclosed polyurethane hydrogels include the following: U.S. Pat. No. 4,241,537 (Wood) discloses a plant growth media comprising a hydrophilic polyurethane gel composition prepared from chain-extended polyols; random copolymerization is preferred with up to 50% propylene oxide units so that the prepolymer will be a liquid at room temperature. U.S. Pat. No. 3,939,123 (Matthews) discloses lightly crosslinked polyurethane polymers of isocyanate terminated prepolymers comprising poly-(ethyleneoxy) glycols with up to 35% of a poly(propyleneoxy) glycol or a poly(butyleneoxy) glycol. In producing the Matthews polymer, an organic polyamine is used as a crosslinking agent. The Matthews prepolymers form a cross-linked, three dimensional structure when polymerized as taught in the patent. U.S. Pat. No. 4,182,827 (Jones) discloses a similar use of polyamines in the formation of polyurethane hydrogels.

B. Prior Art Modified Prepolymers and Resulting Polymers

Several types of compounds have been reacted with prepolymers or with matrix bases to act as spacing or coupling compounds in the attachment or immobilization of biologically active agents. For example, U.S. Pat. No. 4,226,935 (Fusee) discloses reacting an amino acid and/or a protein with an excess of a urethane prepolymer, curing the resulting product to form a polymer matrix and coupling an enzyme thereto by use of a carbodiimide. U.S. Pat. No. 4,177,038 (Biebricher et al.) teaches the use of spacers which may be diamines, amino-alcohols or diols.

Modified polyurethane polymers also have been prepared. U.S. Pat. No. 4,439,585 (Gould et al.) teaches a polyurethane diacrylate composition obtained by reacting a diacrylate in the presence of a hydrophilic polyurethane resin. U.S. Pat. No. 4,485,227 (Fox) discloses a poly-(etherurethane-urea) prepared by condensations of a prepolymer with primary diamines, then with an amine-reacting agent. U.S. Pat. No. 4,569,981 (Wenzel et al.) discloses water-dispersible plastics precursors based on isocyanate-terminated prepolymers which have been hydrophilically modified with ionic groups and/or ethylene oxide groups.

Prior Art Cell Growth Enhancers

The prior art of cell growth enhancers and antibody production stimulators discloses numerous compositions. These compositions are the result of attempts to reduce the amount of arrival serum present in the media or eliminate its presence all together in order to solve problems well known in the art, e.g. contamination by animal pathogens, cell growth inhibition, etc. However, serum also proves to be quite useful in promoting cell growth and provides a favorable environment for cells to maximize their antibody production. Thus the attempt to delete serum has led to attempts to substitute serum with other media additives which are just as beneficial.

For instance, Schacter discloses in "Serum-Free Medium for Growth Factor- Dependent and - Independent Plasmacytomas and Hybridomas", *Journal of Immunological Methods*, Vol. 99, pp. 259–270 (1987), media which contains cell growth additives such as L-glutamine, beta-mercaptoethanol, Hepes buffer, glutathione, sodium selenite and sodium pyruvate. Transferrin (human, iron-saturated), albumin (bovine serum, BSA), soybean lipids, and low density lipoproteins (LDL), were also added prior to subculture. Schacter discloses other common growth factors for plasmacytomas and hybridomas to be: linoleic acid coupled with fatty acid-free BSA, insulin, hydrocortisone, prostaglandin E$_2$, catalase, ascorbic acid, SGF-9, ethanolamine and putrescine.

Velez et al in "Kinetics of Monoclonal Antibody Production in Low Serum Growth Medium", *Journal of Immunological Methods*, Vol. 86, pp. 45–52 (1986) disclose a cell growth medium (Dulbecco's Modified Eagle Medium) containing Primatone RL, Pluronic F-68, and 1% fetal bovine serum. Velez et al. disclose that Primatone RL is a protein hydrolysate and Pluronic F-68 is a block copolymer of polyoxypropylene and polyoxyethylene. They disclose that cell growth in the presence of these components is equal to cell growth experienced in media containing 5% fetal bovine serum.

PCT Application No. AV87/00248 discloses serum-free tissue culture media containing polymeric materials comprising ethylene oxide (EO) and propylene oxide (PO) components. Specifically, Pluriol PE 6800, an EO and PO based polyol, was used in serum-free medium for the production of human growth hormone (hGH) in an aerated reaction vessel. This application discloses that the alkylene oxide polymer is particularly useful in the cultivation of cells requiring attachment because it appears that the polymer acts as a cell protective agent which prevents the disassociation of the cells from the support medium as well as the lysis of cells when they are exposed to aeration. It has been found that cells requiring attachment grow better when they are agglomerated.

European Patent Application No. 248,656 discloses a composition for cell cultivation wherein the composition contains, among other additives, a polyethylene glycol, polyvinyl alcohol and polypropylene glycol, and, optionally, a low density lipoprotein (LDL).

Mizrahi discloses in "Primatone RL in Mammalian Cell Culture Media", *Biotechnology and Bioengineering*, Vol. 19, pp. 1557–1561 (1977) the use of Primatone RL in RPMI 1640 basal media for growth of lymphocytes. As mentioned earlier, Primatone RL is a protein hydrolysate. Mizrahi discloses that Primatone must be used in conjunction with at least 1% fetal calf serum.

In "Pluronic Polyols in Human Lymphocyte Cell Line Cultures," *Journal of Clinical Microbiology*, Volume 2, pp. 11–13 (July 1975), Mizrahi also discloses the use of polyoxypropylene/polyoxyethylene condensates in mammalian cell culture media. As mentioned earlier, the polyol condensates used were the Pl F68, F77, F88 and Fl108 polyols of the pluronic series from BASF (Wyandotte Corp.) Mizrahi shows that in the presence of 0.05 and 0.1% F68 and F88 polyols, cell yields equalled or bettered that obtained in the basal media. However, at 0.2% of F68 and F88, as well as 0.05 to 0.2% of F77 and Fl108, growth inhibition occurred.

However, as far as the applicants are aware there has been no teaching on the use of modified prepolymers or polymers wherein the prepolymer or polymer is an isocyanate-capped alcohol or polyol.

SUMMARY OF THE INVENTION

The cell growth enhancer and antibody production stimulator of this invention are the result of a polyurethane polymer system which provides modified prepolymers and polymers. The cell growth enhancers of this invention are prepared by modifying or derivatizing isocyanate end-capped polyols in aqueous or organic solutions. Particularly suitable polyols are those substantially or exclusively comprising ethylene oxide units. The polyols are then capped with isocyanate (NCO) groups, which are in turn modified so that a free amino, sulfonic acid or sulfhydryl functional group is expressed on the modified prepolymer or polymer.

There are basically two routes of production for the modified prepolymer or polymer which make up the claimed cell growth enhancer and antibody production stimulator. First, modified hydrated polymers may take the form of water-swellable, three-dimensional hydrogels or foams. Subsequently, the gels can be dissolved and the resultant preparation of water soluble polymeric units can be added to cultured cells to produce the effects of this invention. Similarly, the hydrated polymers may take the form of a dense or thin coating or impregnant on a substrate, including, under dilute conditions, a monomolecular or substantially monomolecular layer. The coatings and impregnates of this invention are considered gels or hydrogels and are included by those terms unless otherwise noted. The terms gel and hydrogel are meant to refer to polymers which are substantially non-foamed in structure. For various reasons, the resulting gels may not be all "gel" and some foam may be present.

In a second embodiment, higher proportions of the isocyanates of the prepolymer are modified, thus yielding individual modified prepolymer molecules which are water soluble and which are usually incapable of forming a polymeric structure. However, some polymerization may occur, thus resulting in modified polymeric units. Accordingly, the second route produces water soluble units which are mostly prepolymeric, but will also comprise polymeric units.

In certain instances, a third method of synthesis produces a cell growth enhancer, which, upon subsequent chemical modification, not only enhances cell growth, but also stimulates antibody production. As discussed later, when an isocyanate capped prepolymer is modified by disulfide containing compounds bearing an amino group, such as cystamine, subsequent reduction of the disulfide bond results in modified prepolymer or polymer which stimulates antibody production. In otherwords, in certain circumstances, a cell growth enhancer produced by one of the first two routes can be an intermediate or starting material for the third production route which provides an antibody production stimulator.

Therefore, it is a particular purpose of this invention to provide a novel growth enhancer and/or antibody production stimulator from novel modified prepolymers and polymers.

It is also an object of this invention to provide a cell growth enhancer which is adaptable to be an antibody production stimulator.

It is a further object to produce cell growth enhancers and antibody production stimulators which provide greater growth enhancement and antibody stimulation than that obtained by the prior art compositions.

Finally it is an object to produce cell growth enhancers and antibody production stimulators from compounds which do not possess these effects. This is specifically effective when non-reactive prepolymers undergo the claimed modification or derivatization reaction.

DETAILED DESCRIPTION OF THE INVENTION

The cell growth enhancer and antibody production stimulator of this invention comprise a new class of modified hydrophilic polyurea-urethane prepolymers and related modified polymers. The cell growth enhancement and antibody production stimulation is due to the addition of specific functional groups to the prepolymer molecule. The prepolymers from which the modified compounds can be prepared are oxyethylene-based alcohols which include monofunctional alcohols, diol or polyol units with some or essentially all of the hydroxyl groups of the alcohols capped with polyisocyanate. The prepolymer is modified or derivatized by reaction with a compound having at least one isocyanate (NCO) reactive functional group. The terms "modified" and "derivatized" will be used interchangeably herein. The modifying compound also has a second functional group which is non-reactive with the NCO groups of the prepolymer or is less reactive, preferably substantially less reactive, with the NCO groups than the NCO-reactive group (that is, than the first functional group). The NCO-reactive group may be a sulfhydryl (—SH), amino (—NH$_2$), or carboxyl (—COOH) group.

Polymerization of partially modified prepolymers in water or an aqueous solution represents the first route of production mentioned earlier and acts to gel the solution or a deposited layer of the composition. Subsequently, the gel is dissolved into water soluble polymeric units. In the second route of production completely modified prepolymer and modified polymeric units are formed. The units are soluble in water and will not form a gel by polymerization through the NCO groups.

Prepolymer Preparation

The prepolymers utilized as cell growth enhancers are prepared from oxyalkylene-based alcohols. These can be diols or polyols, including diols or polyols made up of ethylene oxide monomer units, and to some extent monofunctional alcohols made up of the same monomer units. The proportion of ethylene oxide units may vary, and is described in more detail below. Prepolymers are formed when the diols and/or polyols are end-capped with di- or polyfunctional isocyanates as described below. In certain embodiments (i.e., the second route of production where polymerization is not required), monofunctional alcohols may be end-capped with di- or polyfunctional isocyanates for use in this invention. These compounds are not, strictly speaking, "prepolymers." However, since they are prepared and used in an analogous manner, the term "prepolymer" as used herein will refer to isocyanate-capped monofunctional alcohols as well as diols or polyols.

One extensive class of hydrophilic, isocyanate-capped urethane prepolymer is described in U.S. Pat. No. 4,137,200 (Wood et al.), the teachings of which are incorporated herein. The Wood et al. prepolymers are blends of a monomeric polyol and polyoxyalkylene glycol, the hydroxyl groups of the blend being capped with a polyisocyanate. The polyoxyethylene polyol may have a weight average molecular weight of about 100 to about 20,000, and preferably between about 600 to about 6000, with a hydroxyl functionality of about 2 or greater, preferably from about 2 to about 8. The polyols should desirably have about 40 to about 100 mole percent ethylene oxide content.

It is possible, and may be desirable, to incorporate various amounts of a relatively hydrophobic comonomer. Thus, comonomers such as propylene oxide or butylene oxide may be copolymerized as a random copolymer, block-copolymer, or both. Aliphatic, aromatic or aliphatic-aromatic isocyanates may be used, such as those listed hereinbelow. Optionally, a crosslinking agent may be included.

Another group in this first class of isocyanate-capped urethane prepolymers comprises the isocyanate-capped polyesters. Such prepolymers may be made by condensing a polyhydric alcohol with a polycarboxylic acid to form a linear polyester which is then reacted with a slight molar excess of a polyisocyanate to provide an essentially linear polyurethane having terminal isocyanate groups and having an average molecular weight within the range 100 to 20,000, preferably between about 600 to about 6000. Polyhydric alcohols that can be used in preparing such prepolymers include the polyalkylene glycols such as ethylene, propylene and butylene glycol and polymethylene glycols such as tetramethylene and hexamethylene glycols.

Isocyanate capped polyethers is yet another group which can be used. These prepolymers can be made by reacting, for example, polyalkylene glycols with diisocyanates of the type listed below to provide a polyurethane having terminal isocyanate groups and having an average molecular weight within the range 100 to 20,000, preferably between about 600 to about 6000. Specific examples of these prepolymers are the prepolymers from the HYPOL ™ polyurethane prepolymer series available from Grace Specialty Chemicals Co., W. R. Grace & Co.-Connecticut.

A second class of prepolymers suitable for use in this invention comprises polyoxyalkylene diols or polyols which are of generally higher molecular weights and which are predominantly or exclusively made up of ethylene oxide units. This second class is somewhat more preferred for use in this invention. Preferably, at least 75% of the monomer units should be ethylene oxide, and in some instances, up to 100% ethylene oxide units would be preferable. As specific examples of this class of prepolymers, prepolymers from the BIOPOL ™ polyurethane prepolymer series available from Grace Specialty Chemicals Co., W. R. Grace & Co.-Connecticut, will be particularly suitable. Except for the monofunctional alcohols based prepolymers discussed later, these prepolymers will form hydrogels when partially modified as described below.

High molecular weight ethylene oxide-based monofunctional alcohols, diols and polyols are used to prepare this second class of prepolymers, derivatized prepolymers and hydrated polymers of the present invention. The diol or polyol molecular weight prior to capping with polyisocyanate preferably should be at least about 7000 to 8000 MW, more preferably about 10,000 to about 30,000 MW. If a monofunctional alcohol is used, the molecular weight of the alcohol should be at least 500 to 10,000.

It is preferred to use trihydroxy compounds (triols) in the preparation of the polyols which are the precursors to the prepolymers, derivatized prepolymers and hydrated polymers of this invention. For example, glycerol is a preferred triol. Trimethylolpropane (TMOP), trimethylolethane and triethanolamine are other suitable triols. In addition, tetrols, such as pentaerythritol, may be used to prepare polyols for use in this invention. Triol- or tetrol-based polyols are capped with difunctional or polyfunctional isocyanate compounds as described below to form the prepolymer.

Alternatively, diols of appropriate molecular weight may be used as precursors to the prepolymers of this invention. Diols of appropriate molecular weight are capped with polyfunctional isocyanates as described below to form the prepolymers. High molecular weight polyethylene glycols are particularly useful. Especially desirable in this embodiment are polyethylene glycols of the formula H(OCH$_2$CH$_2$)$_x$OH where x is an average number such that the glycol has an average molecular weight of at least about 7000, preferably about 10,000 to about 30,000. Alternatively, diols may be capped with diisocyanates and used in conjunction with crosslinking compounds to form the hydrated polymers described herein. Crosslinking compounds useful for this purpose include polyfunctional amines and polyfunctional isocyanates. In still another alternative embodiment, diols may be mixed with polyols and the resulting mixture reacted with isocyanates to produce the prepolymer of this invention.

Monofunctional alcohols may be selected as the basic "prepolymer" unit where completely modified prepolymer units are intended. For example, mono-methoxy poly(ethylene glycol) can be used. In this embodiment, the monofunctional alcohol is end-capped with polyisocyanate and then modified according to this invention. These modified compounds are produced under the second route of production and will not be capable of polymerization. Rather, they will result in small, completely modified prepolymer units which are soluble in water.

The prepolymers of the above polyurethane class are formed by reacting the hydroxyl groups of the alcohols described above with polyisocyanates. "Polyisocyanate" as used herein is intended to refer to both diisocyanates and polyisocyanates, as appropriate, except as indicated by specifying the use of difunctional or polyfunctional isocyanates. Thus, isocyanate end-capped (i.e., isocyanate-terminated) prepolymers are formed.

The selected precursor to the prepolymer influences the choice of polyisocyanate in that the prepolymer structure must lend itself to sufficient crosslinking to gel an aqueous prepolymer solution or to form a crosslinked polymeric coating where those properties are desired. In the embodiment in which the precursors to the prepolymers are polyols (that is, triol-based or tetrol-based), difunctional isocyanates are preferred. If desired, polyfunctional isocyanate compounds may also be used with polyols. Mixtures of suitable isocyanates also may be considered.

Where triols are used as the precursors to the prepolymers, they may be reacted with polyfunctional isocyanate compounds to form the prepolymers of this invention. This combination yields prepolymers having sufficient functional groups for crosslinking in the formation of the hydrated polymer. In an alternative embodiment, diols can be used as the precursors to the prepolymers, wherein the diols may be capped with a difunctional isocyanate. However, in order to achieve sufficient crosslinking from these difunctional prepolymers, they are used in conjunction with a crosslinking compound. The preferred crosslinker is trimethylolpropane ("TMOP"), although others may be used. For example, alternative crosslinkers include glycerol, trimethylolethane, pentaerythritol, triethanolamine, polyfunctional amines, polyfunctional isocyanates, and the like.

Aromatic, aliphatic or cycloaliphatic polyisocyanates may be used in any of the above-described embodiments. However, when shaping or handling of the prepolymer becomes a concern, the use of aliphatic polyisocyanates is desirable because aliphatic isocyanate-capped prepolymers typically require about 20 to 90 minutes to gel to a hydrated polymer state.

Examples of suitable di- and polyfunctional isocyanates are found in the following list:
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
4,4'-diphenylmethane diisocyanate
3,3'-dichloro-4,4'-biphenylene diisocyanate
1,6-hexamethylene diisocyanate
1,4-tetramethylene diisocyanate
1,10-decamethylene diisocyanate
cumene-2,4-diisocyanate
1,5-napthalene diisocyanate
methylene dicyclohexyl diisocyanate
1,4-cyclohexylene diisocyanate
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyante
2,4-dimethyl-1,3-phenylene diisocyante
5,6-dimethyl-1,3-phenylene diisocyanate
2,4-diisocyanatodiphenylether
4,4'-diisocyanatodiphenylether
benzidine diisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenylmethane
2,6-dimethyl-4,4'-diisocyanatodiphenyl
2,4-diisocyanatostilbene
3,3'-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate
p,p',p''-triphenylmethane triisocyanate
trifunctional trimer (isocyanurate) of isophorone diisocyanate
trifunctional biuret of hexamethylene diisocyanate
trifunctional trimer (isocyanurate) of hexamethylene diisocyanate
polymeric 4,4'-diphenylmethane diisocyanate When capping the hydroxyl groups of the alcohol, the isocyanate-to-hydroxyl group ratio preferably should be between about 1.8 and about 2.2. Higher ratios may be used but are not preferred since they may lead to problems associated with excessive monomer present in the final products. The capping reaction may be by any convenient method or procedure. For example, the reaction may be carried out at about 20° to about 150° C., under dry nitrogen, for about 2 hours to about 14 days, preferably in the absence of a catalyst. The time period will be a function of the polyisocyanate used and the temperature at which the reaction is conducted.

Where monofunctional alcohols are used as precursors, capping with polyisocyanates to form the prepolymers of this invention is effected using stoichiometric amounts of reactants.

It is preferred to avoid using an excess of polyisocyanate in preparing the prepolymer. Preferably, an isocyanate-to-hydroxyl group ratio of 2:1 (for example, one diisocyanate molecule per hydroxyl group of the polyol) is used to ensure complete end-capping of the polyol. Complete end-capping eliminates excessively high viscosity in the prepolymer by avoiding undue amounts of chain extension. However, a slight excess of isocyanate, i.e., up to about ten percent, can be used.

The preferred polymer system also has a low free isocyanate content. This is achieved by employing high molecular weight polyols and by avoiding excessive quantities of isocyanate in the end-capping reaction so that free isocyanate monomers are unlikely to be present. The isocyanate concentration in the prepolymer should be about 0.1 to about 0.53 milliequivalents per gram for prepolymers formed from diols or polyols of about 7,000 to 30,000 MW, as well as the prepolymers formed from the monofunctional alcohols of about 500 to 10,000 MW.

Further, it is not imperative that all of the hydroxyl groups are end capped. In some instances, e.g. when less than stoichiometric amounts of isocyanate are used, end capping may only occur on substantially less than all of the hydroxy groups; yet there will still be a sufficient number of NCO groups available for modification by the modifying compounds so that the modified prepolymers will result in an effective cell growth enhancer and/or antibody production stimulator.

Notwithstanding a preference for low isocyanate content, the preferred polymer system described herein affords a greater degree of flexibility in this regard than conventional systems, because this system can be used with an organic solvent. The presence of an organic solvent in preparing and handling the prepolymer protects against excessive viscosity resulting from the use of polyols of higher molecular weight or increased EO content, or from the use of insufficient quantities of isocyanate for complete end-capping of the diol or polyol. That is, the organic solvent permits the use of less than stoichiometric (2:1) quantities of the isocyanate monomer. Chain extension resulting from incomplete end-capping typically results in increased viscosity which may make handling of the prepolymer difficult or impossible. By contrast, the system used in this invention tends not to be affected negatively by increased viscosity due to chain extension, or from any other cause, because the solvent serves to maintain the viscosity within a range suitable for convenient handling of the prepolymer.

The organic solvent used in preparing the prepolymer must be compatible with the reactants. Primarily, the solvent must be one in which the monofunctional alcohol, diol or polyol and/or prepolymer can be readily dissolved, preferably at ambient temperatures. Suitable solvents for preparing the prepolymer include acetonitrile, dimethyl formamide, dimethyl sulfoxide, tetrahydrofuran, dioxane, dichloromethane, acetone and methyl ethyl ketone, or mixtures thereof. Acetonitrile is preferred.

In one embodiment using an organic solvent, the alcohol, diol or polyol itself is dissolved in the solvent and is reacted with polyisocyanate while in solution to yield the isocyanate end-capped prepolymer. This embodiment is particularly preferred where the diol or polyol is solid or crystalline at ambient temperatures, that is, for diols or polyols substantially or exclusively comprising ethylene oxide units and for high molecular weight diols or polyols. In this manner, even crystalline diols or polyols can easily be handled without heating to their respective melting points. Even though the prepolymer formation reaction is conducted at elevated temperatures, utilizing an organic solvent to first place the diol or polyol in liquid form assures good reaction and prepolymer formation.

In another embodiment using an organic solvent, the isocyanate end-capped prepolymer first is prepared and then is dissolved in an organic solvent. This embodiment will be useful where the diol or polyol already is liquid or pasty at ambient temperatures and does not require dissolution in order to prepare the prepolymer. For example, diols or polyols of lower molecular weight or higher propylene oxide or butylene oxide content may be treated in this manner. Use of a solvent at the prepolymer stage is advantageous where increased viscosity occurs due to chain extension of incompletely end-capped diols or polyols. When using organic solvents the solvent will need to be removed before the modified prepolymer or polymer is added to enhance cell growth.

It may be desired to add an antioxidation agent, preferably prior to preparation of the prepolymer. Antioxidants are not required to make or use the prepolymers or polymers of this invention. However, storage and handling properties may be enhanced by such an addition by preventing oxidative breakdown of the polymer or its precursors. Suitable antioxidants include the hindered phenolic compounds. Specific examples are Irganox TM (Ciba-Geigy Corp.) and Santonox TM (Monsanto Chemical Co.). The antioxidant may be added in amounts of about 0.01 to about 1.0%, preferably about 0.02 to about 0.1%, based on the weight of the polyol or precursor to the prepolymer.

Modifying Compounds

The cell growth enhancer and antibody production stimulator is prepared by modifying the above described prepolymers. The prepolymers are modified or derivatized so that they express sulfhydryl, sulfonic acid or amino functional groups. The combination of these functional groups with the ethylene oxide based polyols provide cell growth enhancement and antibody stimulation characteristics to the basic prepolymer and polymeric compounds, as well as to the modifying compounds. Accordingly, specific functionality and reactivity can be imparted to noneffective or marginally effective cell growth promoters and/or antibody production stimulators, as well as impart reactivity to an otherwise nonreactive, biocompatible polymer. For example when polymerized structures are formed, the surface of the polymer may be generally nonadsorptive and nonreactive with the exception of the desired functionality inserted into the polymer by the process described herein.

The prepolymer is modified by reacting it with a compound containing at least one isocyanate (NCO) reactive functional group. Accordingly, the NCO reactive functional group acts as the attachment point between the prepolymer and the modifying compound. The modifying compound also has a second functional group which may be isocyanate reactive, but is preferably less reactive so that the isocyanates are modified by the first NCO reactive functional group. Upon modification of the isocyanate group, a "free" functional group is expressed. The free functional group expressed can be the second, less NCO-reactive, functional group or as discussed below, can be a functional group expressed as the result of an internal linkage being reduced or broken. In the examples below the disulfide bond in cystamine is reduced to express a sulfhydryl. Specific examples of the free functional group include amino, sulfonic acid and sulfhydryl. Once the prepolymer is modified to express a free functional group the desired effect is achieved. For instance, when the free functional group is an amino, the free functional group in combination with the other chemical moieties acts to increase cell reproduction anywhere from 40 to 100% in cultured media. In other instances, e.g. when the modified prepolymer or polymer expresses —SH, the modified prepolymer or resulting polymer increases antibody production of immunological cells up to 4–5 fold.

As mentioned earlier, the NCO-reactive functional group is a sulfhydryl (—SH), amino (—NH$_2$) or carboxyl (—COOH) group. In some instances, compounds having other functional groups such as hydroxyl groups may sometimes be used. Isocyanate modification by these functional groups are not a preferred route and will not be discussed herein.

The rate and extent of the modification reaction will depend in part on the NCO reactive functional group of the modifying compound and, in part, on the relative molar quantities of the prepolymer and the modifying compound.

In general, sulfhydryl groups react preferentially and rapidly with the isocyanate groups of the prepolymers when the reaction proceeds under conditions which cause formation of the thiolate ion, as described below. The thiolate ion reacts with the isocyanate groups of the prepolymer to provide modified prepolymers containing —NHC(O)S— (thiourethane) linkages, even in the presence of amino, hydroxyl or carboxyl functional groups. Thus, when a thiolate ion (—S$^-$) is present, an amino group is rendered virtually non-reactive, thus allowing —S$^-$ to modify the NCO groups. Where the NCO reactive functional group is an amino group contained in a diamine or polyamine compound or is in the presence of a carboxyl group, a large molar excess of the modifying compound is used so that substantially all of the isocyanate groups of the prepolymers are modified by the amino group.

However, isocyanate-capped prepolymers will react substantially faster with sulfhydryl-containing compounds than with the compounds containing the other listed groups only when reacted under conditions in which the thiolate anion (—S$^-$) is formed as the active species. Consequently, under conditions where a sulfhydryl-containing compound will not readily form the thiolate reactive group, the prepolymer modification reaction will proceed very slowly and may not occur to any appreciable extent. That is, the presence of the sulfhydryl group alone is not sufficient for the modification reaction in the absence of suitable conditions to form the thiolate ion. For example, reaction of prepolymer and ethanethiol (C$_2$H$_5$SH) in acetonitrile solvent will not proceed in the absence of a catalyst to ionize the sulfhydryl group of ethanethiol. Nevertheless, even in circumstances where the thiolate is present, there will be some reaction between the amino and NCO groups. Further, reaction conditions may vary so that a thiolate will not be present during portions of the reaction, thus increasing the chance that amino groups will react with the NCO groups.

The thiolate anion may be formed catalytically by the addition of a catalyst. Suitable catalysts would include base catalysts (preferably a tertiary amine such as triethylamine or N-methyl imidazole) or reducing agents, such as sodium borohydride. In certain cases, intramolecular or self-catalysis may occur to cause formation of the thiolate ion.

As illustrated below, an example of a compound undergoing intramolecular catalysis is cysteamine, formed by treating cystamine ((NH$_2$CH$_2$CH$_2$)$_2$S$_2$) with a reducing agent.

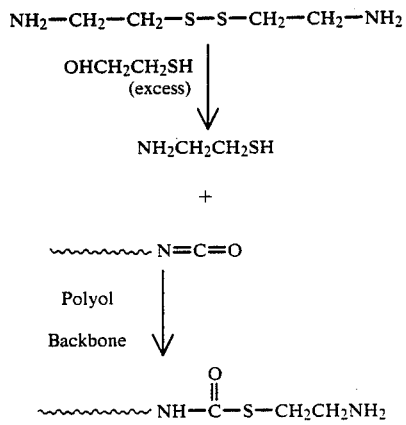

Specifically, in the presence of mercaptoethanol (HOCH$_2$CH$_2$SH) or another reducing agent, the disulfide bond of cystamine is reduced to form cysteamine (NH$_2$CH$_2$CH$_2$SH) which contains both a free amino and a free sulfhydryl group. The amino and sulfhydryl groups of the cysteamine molecule interact to cause formation of the thiolate ion by intramolecular catalysis. The NCO groups of the prepolymer react preferentially with the thiolate group of the self-catalyzed cysteamine molecule, yielding a prepolymer modified via the thiolate so as to have a free amino group which corresponds with the free functional group which is expressed by the modified prepolymer.

The above reaction mechanism is supported by NMR analysis. This analysis indicates that upon formation of a thiolate ion and its reaction with a NCO group, a peak appears for a NHC(O)—S—CH$_2$— linkage.

Specifically, characteristic peaks for NCO, NHC(O)—S—CH$_2$— and NHC(O)—NH were first established by reacting IPDI with ethanethiol, glycol, ethanol and aminoethanol. The products were analyzed to determine the adducts formed and to determine the chemical shifts of the reacted carbonyl carbons. From the NMR study, it appears that the NCO groups of IPDI do not react with the sulfhydryl group of ethanethiol in acetonitrile but an exothermic reaction does occur with the ionized thiolate. This is indicated by NMR analysis conducted after adding a tertiary amine to ionize the thiol group of ethanethiol. For instance, with ethanethiol alone, the N=C=O group of IPDI creates a signal at 123–124 ppm. However, for the thiolate adduct of IPDI, the isocyanate signals disappear, and new signals which are assigned to the carbonyl NHC(O)—S—CH$_2$— group are seen at 166.5–168.0 ppm. From this study the chemical shift of NHC(O)—NH carbonyl carbon is found to be in the range of 160–162 ppm.

The Table below records the above shifts.

TABLE I

Chemical Shift of the Carbonyl Carbons of IPDI Adduct of Various Substrates

| Substrate | Bond | Chemical Shift (ppm) |
|---|---|---|
| — | N=C=O | 123–124 |
| —NH$_2$ | NH—C(O)—NH— | 160–162 |
| —SH | NH—C(O)—S— | 167–168 |

The above pattern is also observed in the NMR analysis of the unmodified prepolymer and the cystamine derivative of the prepolymer. The carbon-13 NMR spectrum of the unmodified prepolymer, which is a 1:3 mole adduct of polyether triol and IPDI, indicates the presence of N=C=O and NHC(O)—O— carbonyl carbons. On the other hand, the carbon-13 NMR spectrum of the thiolate (cysteamine) modified prepolymer which was prepared in the presence of 2-mercaptoethanol, shows the new carbonyl carbon signals in the chemical shift range of the thiourethane linkage.

Alternatively, as shown below, cystamine itself can be reacted with the prepolymer prior to reduction of the disulfide bond, thus leaving the NCO group to be modified by an amino group (—NH$_2$).

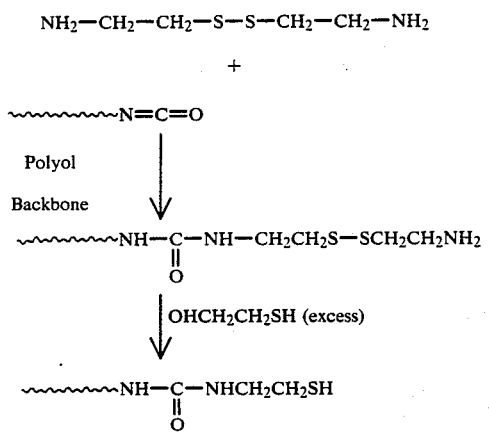

Accordingly, both the NCO reactive functional group and the free functional group expressed on the modified prepolymer are —NH$_2$. However, as mentioned earlier, the free functional group can be changed by reducing the disulfide bond in cystamine. For example, upon reducing the disulfide bond, the free functional group will be expressed as a sulfhydryl.

As also discussed earlier, the above is an example of the third production route where the claimed cell growth enhancer can be altered and adapted to become an antibody production stimulator. For instance, following modification of the prepolymer with cystamine, a reducing agent, such as mercaptoethanol, is added to reduce the disulfide bond, thus allowing the sulfhydryl group to be expressed on the prepolymer. It is only after the disulfide bond is reduced that the S is expressed. Carbon-13 NMR spectrum of the prepolymer-cystamine adduct with no prereduction with 2-mercaptoethanol shows signals at 160 ppm which is consistent with the reaction of the NCO groups with the —NH$_2$ group in cystamine to from the urea linkage (NHC(O)NH—).

Further, reaction of NCO-capped prepolymers with a modifying compound containing an amino group is relatively slower than reaction with thiolate as the NCO reactive functional group, although the reaction rate is still quite rapid. The amino—NCO reaction forms modified prepolymers containing —NHC(O)NH— (urea) linkages. Reaction rates between the prepolymer and modifying compounds containing amino groups will vary with pH. Unprotonated amines are preferred for faster reaction rates.

Where diamines or polyamines are used as the modifying compound, they should be employed in large excess quantities in order to cause modification of the prepolymer. Thus, it is preferred to have more than a 1:1 molar ratio of —NH$_2$ to —NCO groups, preferably greater than 2:1 and most preferably between about 2:1 and about 5:1. It should be understood that use of small amounts of primary or secondary diamines or polyamines will serve the function of crosslinking the modified prepolymer by reacting with the NCO-groups of multiple prepolymer molecules. This is taught in prior patents such as Matthews et al., described above. However, when used in large excess quantities, the polyamines do not serve the crosslinking function, since it is unlikely that any polyamine molecule will react with NCO-groups from more than one prepolymer molecule. Rather, the reaction serves to derivatize the prepolymer in the manner of this invention.

Another category of NCO reactive functional groups useful in forming the modified prepolymers and polymers of this invention includes compounds having carboxyl (—COOH) groups. For example, certain amino-protected amino acids and peptides might be reacted with the prepolymer via the carboxyl group. As another example, 2,2'-dithiodiethanoic acid can be used as the modifying compound. However, the reaction of the prepolymers' NCO-groups with a carboxylic acid is very slow. The reaction rate can be accelerated by the addition of a base, e.g., triethylamine, N-methyl imidazoles, etc. The modified prepolymers will contain anhydride or amide linkages.

As with diamine-or-polyamine modifying compounds, compounds containing carboxyl groups should be employed in large excess quantities in order to modify the prepolymer. By "large excess quantities" is meant greater than 1:1 molar ratio of —COOH to —NCO groups, preferably better than 2:1 and most preferably between 2:1 and about 5:1. When used in these large excess quantities, complete or substantially complete modification of the prepolymer NCO groups occurs.

As disclosed earlier, the modified prepolymers also exhibit cell growth enhancement properties, as well as antibody production stimulation, when the second free, functional group is a sulfonic acid moiety, e.g., taurine. It has been found that sufficient modification occurs at a SO$_3$—: NCO ratio between 1:2 and 1:1. However, there is also no indication that ratios of 2:1 or more would not result in derivatization.

Examples of suitable modifying compounds with which the prepolymer may be reacted according to this invention include the following:

2-aminoethanol (ethanolamine)
aminoethyl hydrogensulfate
aminoethane sulfonic acid (taurine)
L- or DL-cysteine (alpha-amino-beta-thiol propionic acid)
L- or DL-cystine (di(alpha-amino-beta-thiol propionic acid)
L- or DL-cysteinesulfonic acid
L- or DL-cysteic acid cystamine (2,2-dithiobis(ethylamine))
cysteamine (amino ethane thiol)
glutathione
3-amino-1-propane sulfonic acid
p-aminophenyl-1-thio-beta-D-galactose
penicillamine
2,2'-dithiodiethanoic acid
3,3'-dithiodipropionic acid In addition to these specific examples, compounds from the following groups may be used:
peptides with sulfhydryl groups
peptides with free amino groups
polypeptides
animal hormones
carbohydrates
polysaccharides
lipids
nucleic acids
amino sugars
amino acids
amine surfactants
diamine and polyamines (in large excess quantities).

In relation to the discussion on cystamine modification of the prepolymer, it may be desired to temporarily block a more reactive functional group present in the modifying compound in order to ensure that modification of the prepolymer takes place via the desired functional group. This will allow for preparation of the desired modified prepolymer, without contamination from competing modification reactions. For example, where a modifying compound contains both amino and carboxyl groups, it may be desired to block the amino groups to allow modification via the carboxyl groups. Blocking procedures for various functional groups are well known. Following prepolymer modification, the blocked functional group is de-blocked, again by well-known procedures.

Prepolymer Modification Reaction

The reaction between the prepolymer and the modifying compound may be conducted in a variety of ways by manipulating the order of addition (e.g. adding modifying compound to prepolymer versus adding prepolymer to modifying compound) as well as the environment in which the reaction is conducted (i.e., aqueous versus nonaqueous). Further, the degree of prepolymer modification may be controlled by the relative molar quantities of the components.

In one order of addition, the reaction may be commenced by adding the modifying compound to the prepolymer. Preferably, the modifying compound is used in a nonaqueous solution. This will result in relatively low levels of prepolymer modification, although the extent of modification also will be affected by the molar concentrations. It is preferred to use this order of addition where only small degrees of modification are desired. However, this order is not preferred where the modifying compound is a diamine or polyamine since crosslinking would be the predominant reaction, as described in Matthews et al., above. Rather, where diamines or polyamines are used, it is preferred to use them primarily or exclusively as modifying compounds. It is also preferred where the prepolymer is based on a monofunctional alcohol.

Further, this order of addition is not preferred for use with carboxyl group-containing modifying compounds, since only low levels of modification will be achieved. Extensive to complete modification is ensured by using the order of addition described below, and also by using large molar excesses of the modifying compound where that compound is a diamine, polyamine or contains carboxyl groups.

In this second, and preferred order of addition, the modifying compound is again in a nonaqueous solution, but in this case the prepolymer is being added to the modifying compound. Further, in this order of addition, a large molar excess of the modifying compound is used. This is preferable when extensive or complete modification is desired. This order of addition is particularly preferred for use with diamines, polyamines and compounds containing carboxyl groups as the NCO reactive functional group so that the modification reaction occurs prior to any significant amount of polymerization. If crosslinking or polymerization of modified prepolymer of these classes is desired, it should be conducted via alternative chemistry.

The use of a non-aqueous environment is important in the above embodiment because its use avoids simultaneous polymerization. This embodiment is also preferred where a greater degrees of modification is desired and, for example, most preferred where the modifying compound is a diamine or polyamine or contains a carboxyl group. Moreover, this embodiment offers greater control in modifying particular percentages of the prepolymer by controlling the molar ratios.

Further, the prepolymer and the modifying compound are contacted in the solvent under ambient conditions. The concentration of prepolymer can vary greatly, from close to zero to almost 100%, but preferably between about 5.0 to about 50.0% (wt/wt) prepolymer is used. Although it is possible to derivatize the prepolymer in an ambient atmosphere, it will be preferred to conduct the reaction under a dry, inert atmosphere, such as dry nitrogen, in order to preserve the isocyanate groups. At ambient temperatures, the derivatization reaction typically will be complete in up to about one hour. However, it is preferred to allow a longer time for this step (i.e., about 4 to 24 hours) in order to ensure that the reaction has gone to completion.

As an aside, it should be mentioned that the nonaqueous solvents such as those discussed for preparation of the prepolymer may be used in the modification reactions. In addition, solvents such as toluene, 2-propanol, methanol, ethanol, pyridine, and other aprotic solvents may be used. The solvent should be dried prior to use, for example, by drying over molecular sieves. If methanol or ethanol are used, great care should be taken to thoroughly dry the solvent and to avoid storage prior to use. The isocyanate of the prepolymer may react with water present in the solvent rather than reacting with the modifying compound. To this extent, the prepolymer will undergo polymerization rather than derivatization.

In another method of production, modification of the prepolymer takes place simultaneously with polymerization by contacting the prepolymer and modifying compound in the presence of water or another crosslinking agent. For example, an aqueous solution, e.g. saline solution, of the modifying compound may be used. The prepolymer becomes derivatized and also polymerized to some extent, due to the reaction of some of the isocyanate groups with the modifying compound and some with water. The degree of modification is controlled by the quantity of the modifying compound present in relation to the prepolymer, as well as the quantity of water present. Clearly, this embodiment is useful where partial modification is sought and where it is desired that a three-dimensional modified polymeric structure is formed. This embodiment also is useful in those cases where the modifying compound is insoluble in non-aqueous solvents. The one-step modification reaction of this embodiment also may be advantageous in eliminating process operations.

This method of production is also an example of the first production route of the cell growth enhancer and/or antibody production stimulator, in which route an intermediate product is a three dimensional hydrogel. Once the hydrogel is formed, it may be hydrated with a phosphate buffered solution (PBS) (Ca++, Mg++ free preparation of Dulbecco's formulation commercially available from GIBCO) to introduce physiological levels of salts. Subsequent to removing excess PBS, if necessary, a reducing agent such as 2-mercaptoethanol can be added to dissolve the hydrogel by reducing the disulfide bonds of cystamine and, thus exposing the desired, e.g. the free, functional group and producing the final product of the first production route, e.g. water soluble polymeric units.

The degrees of modification by the modifying compound's NCO reactive functional group can be controlled by balancing the relative molar concentrations of modifying compound, prepolymer and water. That is, the prepolymer and the modifying compound are reacted in sufficient quantities to allow for reaction of the desired portion of the isocyanate groups of the prepolymer. These adjustments are within the skill of the art. Ambient conditions may be used for the modification reaction in this embodiment. The method of use of the modified polymer will dictate the desired extent to which the isocyanate groups of the prepolymer are derivatized by reaction with the modifying compound. Anywhere up to 100% of the isocyanate groups may be modified according to this invention.

For instance, modification of up to about 20% to 30% of the NCO groups will yield a modified prepolymer capable of significant polymerization. Under polymerizing conditions (that is, on exposure to water) the three-dimensional, highly crosslinked structure, e.g. a foam or a gel, of the first production route will be obtained. Whether a gel or foam is formed depends on the prepolymer selected. Such selection is well within the knowledge and ability of a person of ordinary skill in the art. Subsequently, the gel can be dissolved to form the polymeric units used to enhance cell growth and stimulate antibody production.

Conversely, all or most of the isocyanate groups of the prepolymer may be derivatized, yielding the second production route which creates a modified prepolymer which is either incapable of substantial polymerization or can form a stable, three-dimensional structure. Specifically, where greater than about 50% (up to 100%) of the NCO groups are modified, little or no polymerization will occur under polymerizing conditions. Accordingly, this process is a direct synthesis (with no hydrogel product) of the claimed composition with the composition essentially remaining in the form of modified prepolymer units.

Where there is less than total (100%) modification, some crosslinking may occur on exposure to water, yielding small isolated modified polymeric units. Further, the modified polymer units, as well as the modified prepolymeric units discussed above, are soluble in aqueous solutions. However, as mentioned earlier, it is not possible to form a gel or polymer from these modified units except where the polymerization is through other chemistries. However, it should be clear that insufficient NCO-groups will remain for substantial polymerization through isocyanate chemistry. It is in this range (i.e., greater than about 50% modification) that diamine-polyamine-, or aliphatic carboxyl- modified prepolymers are prepared, as well as prepolymers based on monofunctional alcohols.

Modification in the middle range, that is, greater than about 20% t 30% and less than about 50% of the prepolymer isocyanate groups, also can be made according to this invention. See Taurine modified prepolymer in Example XXV where about 50% of the NCO groups were modified. Under polymerizing conditions, polymer strands or chains may form, increasing the viscosity of the modified preparation, although it is unlikely that a stable gel or foam will form. At this extent of modification, the modified polymer or prepolymer typically will be characterized by solubility in, rather than reactivity with, water. However, while at the lower end of the modification range some gelling or foaming will occur, in general, gelling or foaming will occur only where less than about one-third of the terminal NCO groups of the prepolymer are modified.

Polymerization

As previously described, where up to about one-third of the isocyanate groups of the prepolymer are modified, polymerization may be accomplished by the addition of a stoichiometric excess of water or aqueous solution relative to the total remaining available isocyanate groups. Where the prepolymer has been modified to a greater extent, "polymerization" is somewhat of a misnomer, although the composition may be cured by final treatment of the modified prepolymer with water or an aqueous solution. In this case, the remaining isocyanate groups on the modified prepolymer are reacted with water to cure the modified composition, although little or no polymerization occurs due to the high percentage of NCO groups which have undergone reaction with the modifying compound. Any remaining NCO groups react with the water. Alternatively, the remaining NCO groups could be used to couple the modified prepolymer to a surface or to another compound.

In preparing an aqueous solution containing the prepolymer, the prepolymer-to-solution ratio should be about 1:1 to about 1:20, preferably about 1:5 to about 1:15. Setting time increases as the proportion of prepolymer in the aqueous solution decreases. The solution should be stirred or agitated until completely mixed and then allowed to stand so that a three-dimensional modified polymer structure may form.

Polymerization begins to occur spontaneously with formation of urea linkages upon contact of the unmodified isocyanate groups with water. Catalysts or crosslinking agents are not required but are considered optional and may be used if desired. Suitable catalysts include organic tin salts (e.g., dibutyltin dilaurate) and tertiary amines. Suitable crosslinking agents include primary and secondary polyamines and polyfunctional isocyanates.

The modified polymer continues curing until the chemical reaction of all residual isocyanate groups with water is complete or approaches completion. The complete curing reaction may take hours, days or weeks, depending on the conditions and the polyisocyanate used, although it is essentially complete in about four to twenty-four hours. The curing time may be shortened by addition of chain terminating or inactivation agents, such as ethanolamine, which cause end-capping without chain extension.

If an organic solvent is used in the preparation of the prepolymer, modified prepolymer or modified polymer, it most frequently will be removed prior to use of the modified compounds for cell growth enhancement or antibody production stimulation.

Cell Growth Enhancement Properties

As mentioned earlier, the cell growth enhancers from either of the two production routes are water soluble. After solutions of these polymeric units have been dialyzed and filter sterilized, the cell growth enhancer and/or antibody production stimulator is ready for addition to cell culture media for most lymphoid type cells and lymphoid derived cell lines such as B-cell secreting hybridomas.

The experiments in the following examples employ HFN 7.1 hybridoma cells. Serum-free media such as WRC 935 TM media (Amicon) containing insulin, transferrin and albumin was used, as well as a mixture of DME and F-12 media (GIBCO). However, the claimed cell growth enhancer and antibody production stimulator can be used in serum-containing media, especially in situations where a media contains serum to accomodate certain cell lines. The cell growth enhancer is generally used in concentrations between 10 and 50 $\mu$g/ml (mg/l) or between 1 and 7 $\mu$M, depending on the cell line and medium used.

As shown in Table II in the examples, the cell growth enhancer preparation elicits up to a 2-fold increase in cell numbers. Other known lymphocytic cell lines in which this additive might be used are those derived from mammals such as human, mouse, rat, bovine, hamster and the like, such as normal lymphocyte, myeloma cells, B-lymphoblastoid cell, T-lymphocyte leukemia cell and the like, a variety of hybridomas such as mouse hybridoma, mouse-human heterohybridoma, human hybridoma and the like, normal dipoid cells such as fibroblast and the like, a variety of other adherent cells and the like. In addition, the claimed preparation may also be used in avian or insect cell line cultures.

More particularly, the human lymphocytic cells include Namalva ATCC 1432 (Human lymphoblastoid Burkitt lymphoma) (International Journal of Cancer, 12:396–408, 1973); Raji ATCC CCL 86 (Burkitt lymphoma, Human) (Lancet, 1:238, 1964); EB-3 ATCC CCL 85 (Burkitt lymphoma, Human) (Lancet, 1:252, 1964); WL-L2 (Cancer, 22:517, 1968); Daudi ATCC CCL 213 (Burkitt lymphoma, Human) (Cancer Research, 28: 1300-1310, 1968); RPMI 8226 ATCC CCL 155 (Myeloma, Human) (Proceedings of the Society for Experimental Biology and Medicine, 125: 1246-1250, 1967); CCRF-CEM ATCC CCL 119 (Peripheral blood, Human; Acute lymphoblastic leukemia) (Cancer, 18: 522-529, 1965); RPMI 1788 ATCC CCL 156 (Peripheral blood, Human) (IgM secreting) (Journal of the National Cancer Institute (United States), 43: 1119-1128, 1969); CRCF-SB ATCC CCL 120 (Peripheral Blood, Human; Acute lymphoblastic leukemia) (Cancer Research, 27: 2479-2482, 1967); Jurkat (Immunogenetics, 10:247, 1980) and the like. Mouse lymphocytic cells include, for example, MPC-11 ATCC CCL 167 (Myeloma, Mouse) (Immunoglobulin secreting) (The Journal of Experimental Medicine, 131: 515-541, 1970); P3/NS1/-Ag41 (NS-1) ATCC TIB 18 (Non-secreting mouse myeloma) (European Journal of Immunology, 6:511, 1976); P3X63Ag8U.1(P3U1) ATCC CRL 1597 (Mouse myeloma) (Current Topics of Microbiology and Immunology, 81:1-7, 1978) and the like.

Hybridomas include, for example, mouse hybridoma CEA (Text for 2nd Symposium on Research and Development Project of Basic Technology for Future Industries, 175, 1984), HS-II (Ibid.), E235163 (Hybridoma, 4:47, 1985), mouse human-human heterohybridoma N12–16.63 (Text for 2nd Symposium on Research and Development Project of Basic Technology for Future Industries, 175, 1984), high productive strains derived from N12-16.63 such as N12-16.63.49.19, N12-16.63.49.19.69 and the like (Text for 3rd Symposium on Research and Development Project for Basic Technology for Future Industries, 155, 1985), 112-22.25 (Biochemical and Biophysical Research Communication, 129: 26, 1985); HB III-43.1 (Ibid), and the like. The adherent cells include, for example, FL ATCC CCL 62 (Amnion, Human, HeLa Markers), (Proceedings of the Society for Experimental and Biology Medicine, 94: 523, 1957); HeLa ATCC CCL 2 (Epitheloid carcinoma, cervix, Human) (Cancer Research, 12: 264, 1952); WISH ATCC CCL 25 (Amnion, Human, HeLa Markers) (Experimental Cell Research, 23: 14, 1961); CHO-K1 ATCC CCL 61 (Ovary, Chinese hamster, *Cricetulus griseus*) (The Journal of Experimental Medicine, 108: 945, 1958); NCTC clone 929 ATCC CCL 1 (Connective tissue, Mouse), Clone of strain L (Journal of National Cancer Institute (U.S.A.), 9: 229, 1948) and the like.

Further, it appears that the effectiveness of the claimed compounds resides in the combination of chemical moieties. For example, the modified prepolymers involve polyols, isocyanates and the expressed second functional group, e.g. sulfhydryl, amino or sulfonic acid groups. Preferably, the prepolymer resulting from these moieties are 75% ethylene oxide based polyols that have been end-capped with isocyanates such as isophorone diisocyanate and the NCO's have been reacted with modifying compounds containing th above mentioned functional groups.

However, as Table VI and Experiments B and C of Table VII below demonstrate, the cell growth activity is only exhibited when the combination of the above mentioned moieties are present as opposed to the individual presence of polyether polyol and/or the modifying compound. Further, modified prepolymers which are lacking only in the polyol moiety do not enhance cell growth at the same level produced by the derivatives. These results are supported by an additional set of results in Table VIA wherein a different polyol and modified derivative were tested.

The increase in antibody production also does not appear to be the result of a single component. As shown in Experiment A of Table VII, addition of polyols alone to the culture medium produced no marked increase in antibody production on a per cell basis, as well as any significant cell proliferation.

Summary of the Advantages of the Cell Growth Enhancer Compounds

The properties of the modified prepolymers and polymers described herein are unique and offer significant advantages over conventional cell growth enhancers-/antibody production stimulators and general polymer systems.

Firstly, in one embodiment the claimed cell growth enhancer comes in the form of a gel. As discussed earlier the prepolymers and modified prepolymers of this invention have the ability to gel large amounts of water. As discussed above, when only up to about 30% of the prepolymer NCO groups are modified, the modified prepolymers have substantial polymerization capacity. The general nature of the resulting hydrogel will be based on the original prepolymer but will also be influenced by the modifying compound. Thus, when it is expedient to have a gel growth enhancer in the form of a gel, the claimed invention is flexible to meet this need.

Secondly, the cystamine embodiment provides a cell growth enhancer which can easily be adapted to be an antibody production stimulator. Specifically, one can use half the supply of a batch of cystamine modified prepolymer or polymer as a cell growth enhancer; and then reduce cystamine's disulfide bond on the other half to stimulate antibody production. As shown in Example XXVI and Table II, cystamine is used to modify the prepolymer and is later reduced to expose the —SH group, the modified prepolymer increases antibody production 4-5 fold per cell. In total, a 9 fold increase is obtained when combined with the 2 fold increase in the amount of antibody producing cells. Antibody production is also exhibited by derivatives expressing sulfonic acid. See taurine modified prepolymer in Example XXXIV.

Modification of only a limited number of prepolymer isocyanate groups with polyfunctional compounds in this manner permits the introduction of functional or reactive groups while it also maintains the ability of the prepolymer to undergo chain extension and polymerization by reacting with water or a crosslinking agent. A modified, but still biocompatible polymer can thus be formed.

Thirdly, the cell growth enhancer can also be used to supplement media used for cell culture methodologies in which cells are initiated at various low cell densities e.g. 1-1000 cells per milliliter. Cell cloning is just one example of these methodologies in which the claimed enhancer can be used.

The examples which follow are given for illustrative purposes and are not meant to limit the invention described herein. The following abbreviations have been used throughout in describing the invention.

° C.—degrees Centigrade
cm—centimeter(s)
DMEM—Dulbecco's Modified Eagle's Medium
DI—deionized
gm or g—gram(s)
Hg—mercury
IDPI—isophorone diisocyanate
l—liter
M—molar
$m^2$—square meter(s)
meq—milliequivalent(s)
mg—milligram(s)
min—minute(s)
ml—milliliter(s)
mm—millimeter(s)
mmoles—millimoles
μgm or μg—microgram(s)
μm—micrometer(s)
μM—micromolar
MW—molecular weight
N—normal
NCO—isocyanate
ngm—nanogram(s)
PBS—phosphate buffered saline
ppm—parts per million
%—percent
SE—standard error
TM—trademark
v—volume
wt—weight Preparation of the Polyol-Based Prepolymer

EXAMPLE I (Preparation of Prepolymer A)

The polyol used to prepare the prepolymers of this invention, Pluracol V7 TM (BASF), a 7000 MW triol copolymer of ethylene oxide (75%) and propylene oxide (25%), was deionized and dried. Following this deionzation procedure, 1687.46 gm Pluracol V7 was mixed with 165.0 gm isophorone diisocyanate (IDPI) and 0.93 gm Santonox R TM (Monsanto Chemical Co.) and heated at 70° C. under dry nitrogen. Isocyanate levels were determined by addition of dibutylamine and back titration with standard acid. Fourteen days were required for the isocyanate concentration to reach 0.47 meq/gm (0.39 meq/gm = theoretical). The resulting prepolymer, designated Prepolymer A, was liquid at room temperature.

EXAMPLE II (Preparation of Prepolymer B)

A prepolymer was formed by mixing 300.0 gm deionized and dried TPEG10000 TM (Union Carbide Corp.) with 22.0 gm IPDI and 0.16 gm Santonox R. TPEG10000 is a 10,000 MW triol prepared from 100% homopolymeric ethylene oxide. The mixture was heated at 70° C. under dry nitrogen as in Example I, until isocyanate values reached 0.36 meq/gm (theoretical=0.28 meq/gm). This prepolymer, designated Prepolymer B, formed a solid when cooled to room temperature.

EXAMPLE III (Preparation of Prepolymer C)

A prepolymer was prepared by dissolving 50.0 gm (0.0125 equiv. hydroxyl) of polyethylene glycol (8000 MW) (Sigma Chemical Co.) in 100 cc (78.2 gm) acetonitrile. To this was added 3.06 gm (0.0275 equiv. isocyanate) isophorone diisocyanate and 0.03 gm Santonox R. The solution was heated to 70° C. under dry nitrogen in a dry, acid-washed glass flask for 14 days. The isocyanate level declined to 0.10 meq/gm at day 14 (theoretical=0.11 meq/gm). The prepolymer forced was designated Prepolymer C and was stored as a 25% solution in acetonitrile.

EXAMPLE IV (Preparation of Prepolymer D)

A prepolymer was prepared by first dissolving 50.0 gm (0.0263 equiv. hydroxyl) polyethylene glycol monomethyl ether (MW 1900) (Polysciences, Inc.) in 100 ml (79.2 gm) acetonitrile. To this solution was added 6.43 gm (0.0578 equiv. isocyanate) isophorone diisocyanate and 0.03 gm Santonox R. The solution was heated under dry nitrogen at 70° C. in an acid-washed glass flask for 8 days, at which time the isocyanate content was 0.15 meq/gm (theoretical =0.23 meq/gm). This prepolymer, designated Prepolymer D, was stored as a 42% solution in acetonitrile.

EXAMPLE V (Preparation of Prepolymer E)

A prepolymer was prepared by mixing 848.8 gm of deionized and dried polyol BASF 1123 (BASF) with 91.6 gm isophorone diisocyanate in a one liter polyethylene bottle at room temperature with mechanical stirring for 30 minutes. Dry nitrogen was purged over the mix and the bottle was sealed with a screw cap and placed in an electric oven at 85° C. After 11 days the reaction was terminated. The product had an isocyanate value of 0.43 meq/gm and a viscosity of 62,000 cps at 25° C. This prepolymer was designated Prepolymer E (low temperature). A prepolymer was prepared in the identical manner except that it was incubated in an electric oven at 125° C. for 2 days. This prepolymer was designated Prepolymer E (high temperature).

EXAMPLE VI (Preparation of Prepolymer F)

Mono-methoxy poly(ethylene glycol) with a molecular weight of 550 (160 gm, 0.291 moles) was mixed with isophorone diisocyanate (69.0 gm, 0.310 moles) in a polyethylene bottle and purged with dry nitrogen. The sample was placed in an oven and the temperature maintained at 70° C. for 20 hours. At that time, the sample was removed and the isocyanate level was determined to be 1.32 meg/gm. This product was labeled Prepolymer F.

EXAMPLE VII (Preparation of Prepolymer G)

A polyether diol was obtained comprising 84% ethylene oxide and 16% propylene oxide, with a molecular weight of 2200 (Takeda). This diol (800 gm, 0.36 moles) was mixed with IPDI (163.4 gm, 0.74 moles) and placed in a polyethylene bottle under dry nitrogen. The sample was heated at 70° C. for 10 days at which time the ioscyanate level was found to be 0.75 meq/gm. The reaction was terminated at this point and the product was stirred under dry nitrogen. The product was labeled Prepolymer G.

EXAMPLE VIII (Preparation of Prepolymer H)

A polyether triol (800 gm, 0.22 moles) comprising 82% ethylene oxide and 18% propylene oxide, with a molecular weight of 3600 (Asahi Glass) was mixed with isophorone diisocyanate (149.1 gm, 0.67 moles) over dry nitrogen and placed in a polyethylene bottle. The sample was heated at 70° C. for 12 days at which time the isocyanate level reached 0.72 meq/gm. The sample was labeled Prepolymer H and was stored under dry nitrogen at 4° C.

MODIFICATION OF PREPOLYMER

EXAMPLE IX (Aminoethanesulfonic Acid Modification of Prepolymer A)

A solution was prepared by dissolving 126.0 mg aminoethanesulfonic acid (taurine) in 10.0 ml of 0.05 M phosphate buffer (pH 7.0). To 4.72 ml of the taurine solution was added 1.18 gm Prepolymer A, followed by thorough mixing. This ratio was equivalent to one mole of taurine amino group per mole of prepolymer NCO group. The soluble modified prepolymer was stirred overnight at room temperature and then dialyzed to remove excess taurine. The modified prepolymer dissolved in water, rather than exhibiting gel-forming properties. The modified prepolymer was characterized by size exclusion chromatography.

EXAMPLE X (Aminoethanesulfonic Acid Modification of Prepolymer E)

To 200.0 ml of a 1:1 solution of 2-propanol:phosphate buffer (0.05 M) (pH 7.0) was added 1.27 gm aminoethanesulfonic acid (taurine). The mixture was stirred at room temperature until the taurine dissolved. With continued stirring, 5.0 gm Prepolymer E (low temperature) (dissolved in 5.0 ml 2-propanol) was added dropwise to the taurine solution. This calculates to be a 2-fold excess of taurine amino group over prepolymer NCO group. The dropwise addition continued for 15 minutes and the reaction was continued overnite at room temperature. The solvent was removed from the reaction mixture with a rotary evaporator under vacuum. The dried residue dissolved completely in 20.0 ml water.

EXAMPLE XI (Characterization Standard:Tyrosine Modification of Prepolymer E)

A solution was prepared by dissolving 1.63 gm L-tyrosine in 100.0 ml water containing 0.1 ml sodium bicarbonate and adjusting the pH to 11-12. A 5.0 gm quantity of Prepolymer E (low temperature) was dissolved in 10.0 ml 2-propanol and added to the tyrosine solution dropwise with stirring. This calculates to be a 5.5-fold excess of tyrosine amino groups over prepolymer NCO groups. The excess tyrosine was removed by dialysis against water.

The dialyzed composition was analyzed by gel filtration chromatography on Sephadex G-25. Tyrosine-modified prepolymer eluted in the excluded volume where the marker blue dextran eluted. Free tyrosine standard eluted at twice that elution volume. The dialyzed composition appeared to be free of unreacted tyrosine by this analysis. The resulting compound served as a standard for characterizing other modified prepolymers.

EXAMPLE XII (Cystamine Modification of Prepolymer E) (Low Temperature)

A solution was prepared by dissolving 37.1 mg cystamine dihydrochloride in 15.0 ml of 50.0 mM sodium borate (pH 8.5). This solution was added to 1.0 gm Prepolymer E (low temperature) and stirred until the Prepolymer E (low temperature) appeared to be dissolved. Formation of gel occurred at room temperature in approximately 12 hours. Excess cystamine was washed away by adding 20.0 ml PBS to the gel and incubating at 31° C. for one hour. The PBS was poured off and the washing procedure was repeated twice.

To the gel, 5.0 ml of 200.0 mM mercaptoethanol solution in PBS was added to reduce the cystamine disulfide bond in order to activate the second functional group of the modifying compound. After 24 hours the gel had partially dissolved and an additional 2.0 ml of 0.1 M mercaptoethanol solution was mixed with 2.0 ml of the gel/solution, to fully dissolve the gel. The solution was then filter sterilized.

EXAMPLE XIII (Cystamine Modification of Prepolymer A)

A solution was prepared by dissolving 74.2 mg cystamine dihydrochloride in 30.0 ml of 50.0 mM sodium bicarbonate (pH 8.5). This calculates to be a 1.06-fold excess of prepolymer NCO groups over cystamine amino groups, for modification of approximately all of the prepolymer NCO groups. Two grams of Prepolymer A were dissolved in the solution, which was then poured into a glass plate to produce a thin layer which gelled in approximately 12 hours.

To reduce the cystamine disulfide bonds and dissolve the gel, 30.0 ml of 55 mM mercaptoethanol was added. The product was then filter sterilized.

EXAMPLE XIV (Cystamine Modification of Prepolymer B)

A solution was prepared by dissolving 1.3 gm cystamine dihydrochloride in 150.0 ml of 50 mM sodium bicarbonate (pH 8.5). To this solution, 10.0 gm Prepolymer B (as a 50% (wt/wt) solution in acetonitrile) was added by stirring. After four hours with stirring, mercaptoethanol was added to reduce the cystamine disulfide bond. After dialysis against distilled water, the product was filter sterilized.

EXAMPLE XV (Cysteamine Modification of Prepolymer E, Low Temperature)

A solution was prepared containing 40.0 mM cystamine dihydrochloride and 55.0 mM 2-mercaptoethanol in 25.0 ml PBS, thereby reducing the internal disulfide bond of cystamine. To the solution, 0.5 gm Prepolymer E (low temperature) was added dropwise with stirring. The solution was stirred overnight at room temperature. Excess cysteamine was removed by dialysis against water. In this Example, the prepolymer modification was via the thiolate group of cysteamine, leaving the amino group as the second functional group. The result was confirmed by NMR analysis.

EXAMPLE XVA (Cystamine Modification of Prepolymer E, High Temperature)

Excess cystamine was added to insure that all the isocyanates on prepolymer E (high temperature) were endcapped. Cystamine, 1.5 g, (Aldrich lot no. 02016cj) was dissolved in 150 mls of 50 mM sodium bicarbonate, pH 8.5. This solution was added to 10 g of prepolymer E (high temperature) and stirred. A gel did not form, therefore the assumption was made that the fourfold excess cystamine capped all the isocyanate groups, thus preventing crosslinking. While stirring, 0.6 mls of mercaptoethanol was added to the cystamine/prepolymer solution to reduce the cystamine to cysteamine. After dialyzing in deionized water, 55 mM mercaptoethanol solution in PBS was added and the mixture was stirred. The product was filter sterilized through a 0.2 micron filter.

EXAMPLE XVI (Cystamine Modification of Prepolymer F)

Monomethoxy poly(ethylene glycol) with a molecular weight of 550 was mixed with a solution prepared by dissolving Fifty microliters of IPDI (Veba-Chemia AG) in 100 ml isopropanol, and then mixing with 100 ml of the borate buffer containing 107 mg cystamine. The solution was vortexed and then placed in the fume hood overnight at room temperature. The solution was then diluted with 425 parts PBS (v/v) and sterilized by 0.2 micron filtration.

EXAMPLE XVII (Cystamine Modification of Prepolymer G)

Prepolymer G (2.50 gm, 1.88 meq NCO) was dissolved in 2.5 ml 2-propanol. Cystamine dihydrochloride (4.22 gm, 18.7 mmoles) was dissolved in 50.0 ml 0.05 M sodium phosphate (pH 7.0), and the pH was readjusted to 7.0 with 1N NaOH. The prepolymer solution was added dropwise with stirring to the cystamine solution. Stirring for 24 hours at room temperature the product was dialyzed against distilled water for 24 hours to remove low molecular weight material, including unreacted cystamine.

EXAMPLE XVIII (Cystamine Modification of Prepolymer H)

Prepolymer H (2.50 gm, 1.79 meq NCO) was dissolved in 2.5 ml 2-propanol. Cystamine dihydrochloride (4.02 gm, 17.9 mmoles) was dissolved in 50.0 ml 0.05 M sodium phosphate (pH 7.0), and the pH was readjusted to 7.0 with 1N NaOH. The prepolymer solution was added dropwise with stirring to the cystamine solution and stirring was continued for 24 hours. The product was then dialyzed against distilled water for 24 hours to remove low molecular weight materials including unreacted cystamine.

EXAMPLE XIX (Cystamine Modification of HYPOL TM Hydrogel)

HYPOL Hydrogel TM polyurethane prepolymer (2.52 gm, 2.02 meq NCO, Grace Speciality Chemicals Co., W. R. Grace & Co.-Conn.) was dissolved in 2.5 ml 2-propanol. Cystamine dihydrochloride (4.54 gm, 20.2 mmoles) was dissolved in 50.0 ml 0.05M sodium phosphate (pH 7.0), and the pH was readjusted to 7.0 with 1N NaOH. The prepolymer solution was added to the cystamine solution dropwise with stirring. Stirring was continued for 24 hours at room temperature at which time the product was dialized for 24 hours against distilled water to remove low molecular weight materials, including unreacted cystamine.

EXAMPLE XX (Cystamine Modification of HYPOL TM X6100)

HYPOL X6100, an experimental hydrophilic urethane prepolymer (50.0 gm, 93 meq NCO) (Grace Speciality Chemicals Co., W. R. Grace & Co.-Connecticut) was added to a solution of cystamine dihydrochloride (10.5 gm, 46.4 mmoles) in 50 mM sodium bicarbonate (pH 7.0). The solution was stirred overnight at room temperature.

EXAMPLE XXI (Cystamine Modification of Prepolymer A)

Forty-five mls of Solution X were mixed with 3 grams of prepolymer A in a 50 ml polypropylene centrifuge tube (Corning), and 5 ml aliquots were placed in each of nine 10 cm bacterial culture plates (Falcon 1029, lot 5191202). The resulting hydrogel was allowed to form overnight. The composition of solution X was as follows:

40 ml of Borate buffer (50 mM, pH 8.5)
642 μl Cystamine stock (563 mg cystamine HCl/5 ml borate buffer)
4.5 ml of 10X PBS (GIBCO 310-4080, lot 11N2256)

The hydrogels were fully hydrated by incubating each gel with 20 ml PBS for four days at about room temperature (22° C.). The excess PBS was then removed, and the hydrogels reduced with 20 mls (ea) of a PBS solution containing 2-mercaptoethanol (ME). The gels were allowed to incubate at room temperature for four days, and the resultant solution was then transferred to 50 ml centrifuge tube for room temperature storage. A gel was prepared with 63 μM 2-mercaptoethanol in PBS, and sterilized via 0.2 micron vacuum filtration.

EXAMPLE XXII (Cystamine Modification of Prepolymer A)

This gel was prepared according to Examples XXI except the hydrogels were formed, hydrated and reduced in aqueous solutions containing no phosphate or sodium chloride.

Specifically, forty-five mls of Cystamine/Borate solution (2.86 ml of freshly prepared 0.5 M Cystamine in borate buffer were added to 97.1 ml borate buffer pH 8.5) was mixed with three grams of Prepolymer A in a 50 ml centrifuge, and then 5 ml aliquots were transferred to 10 cm bacterial culture plates. After seven hours, 20 mls of water were added to each plate, and the plates were placed in the incubator at 37° C. overnight. The excess water was discarded, and 10 ml of 5.7 mM 2-mercaptoethanol was added to each plate. The plates were placed at 37° C. overnight, and the resultant dissolved gel transferred to a 50 ml tube following 0.2 micron vacuum filtration.

EXAMPLE XXIII (Cystamine Modification of Prepolymer D)

A derivative solution was prepared wherein 1 g of the derivative produced according to Example XVI was mixed with 2 mls of borate buffer containing 22.2 mg cystamine. After vortexing and allowing the solution to sit overnight, the resulting derivative solution was diluted with 25 parts PBS (v/v) and filter sterilized.

EXAMPLE XXIV (Cystamine Modification of Prepolymer A)

A water soluble compound containing primary amino groups, e.g. Cystamine (11.29 mg/ml, Sigma), was dissolved in 50 mM phosphate buffer (pH 7.0). A stock solution of prepolymer A from Example I was then prepared by mixing equal weights of the prepolymer and dry acetonitrile. Four mls of the above cystamine solution was then added to the Prepolymer A stock solution.

It is hypothesized that the above should react to form a derivatized-polymer in solution where 100% of prepolymer A's isocyanate groups had formed a urea linkage through the amino group of the compound of interest. After mixing, the polymer-derivative was allowed to cure overnight at room temperature. An aliquot of the derivatized prepolymer (0.19 gms based on amount of prepolymer A) was then diluted with 10 ml of PBS.

Aliquots (5 ml) of this diluted solution of prepolymer derivative were then reduced with 0.1 ml of a 55 mM solution of 2-mercaptoethanol (GIBCO). These preparations were then sterilized by 0.2 micron filtration.

EXAMPLE XXV (Taurine Modification of Prepolymer A)

A derivative was prepared according to Example XXIV except Taurine (2 aminoethanesulfonic acid, 6.24 mg/ml, Sigma) was used as the primary amino compound to derivatize the prepolymer. It is thought that Taurine will react with 50% of the isocyanate groups to form urea linkages.

CELL GROWTH ENHANCEMENT AND ANTIBODY PRODUCTION STIMULATION

EXAMPLE XXVI (Effects of Cystamine Modified Prepolymer A)

Assays utilizing HFN 7.1 hybridoma cells (CRL 1606 murine hybridoma line, ATCC) produce an immunoglobulin (IgG) that binds with fibronectin, and the amount of IgG produced can be quantified by ELISA or HPSEC. The cells of this line were serially cultured for more than six months in a serum-free medium prepared by mixing three parts of DME and one part of F-12 medium (GIBCO). This mixture has a pH of 7.2 at 37° C. and is prepared with 3 mM sodium bicarbonate, and is further supplemented with 25 mM HEPES (Sigma), 5 μg/ml insulin (Sigma), 1 μg/ml iron-saturated transferrin (Miles), 20 μM ethanolamine (Sigma), 30 nM Se (as $Na_2SeO_3$) (Sigma), and 50 μg/ml Bovine serum albumin (Miles).

A stock of this medium containing 20,000 log-phase HFN 7.1 hybridoma cells per milliliter was prepared, and 5 ml aliquots were placed into each of several T-25 tissue culture flasks (Corning). In this quadruplicate analysis two different volumes of either saline (prepared from 10X Dulbecco's PBS, GIBCO) or the derivative from Example XXI were added to these replicate flasks. The flasks were sealed and placed in a 37° C. incubator for four days. The resultant cell concentration was then determined with a Coulter Counter (TM) particle counter (Coulter Electronics), and the amount of antibody produced by the cultured cells determined by ELISA.

As mentioned earlier and disclosed in Table II, the derivative preparation elicited a 2-fold increase in cell number and a 4–5 fold increase in antibody production rate per cell. This yields a nine-fold increase in total antibody production, e.g. twice the number of cells producing antibodies at 4.5 times the control rate.

TABLE II

| Sample | Derivative (mg/l) | # Cells Final/ # Cells Initial Avg. ± SE | IgG (μg)/ Million |
|---|---|---|---|
| Cells | | | |
| 0.1 ml Saline | 0 | 10.6 ± 0.95 | 22.3 |
| 0.1 ml XXI | 0.035 | 21.0 ± 1.96 | 102.3 |
| 0.25 ml Saline | 0 | 9.7 ± 0.35 | 38.2 |

TABLE II-continued

| Sample | Derivative (mg/l) | # Cells Final/ # Cells Initial Avg. ± SE | IgG (μg)/ Million |
|---|---|---|---|
| 0.25 ml XXI | 0.086 | 22.3 ± 2.01 | 99.0 |

EXAMPLE XXVII (Effect of Initial Cell Density on Growth and Response to Cell Growth Enhancer)

In this example, HFN 7.1 cells were again placed in flasks (T-25) containing the medium described in Example XXVI. In this case, the cell density was varied as indicated in Table III. The derivative produced in Example XXI (0.1 ml) was added to the experimental flasks while no further additions were made to control flasks. The flasks were then sealed and placed in the incubator (37° C.) for four days. The final cell concentration was then determined with a Coulter Counter (TM) particle counter.

As demonstrated in Table III, little or no cell growth is observed when the cultures are plated at low initial cell densities in the absence of derivative. However, if the claimed derivative of the invention was added to the cultures, significant cell proliferation was observed. The derivative also enhanced the growth in cultures plated at higher cell densities where significant growth was observed in the control cultures.

TABLE III

| Sample | Cells per Milliliter Initial | Cells per Milliliter Final | Fold Increase in Cell Number |
|---|---|---|---|
| Control | 1290 | 1375 | 1.1 |
| Example XXI | 1290 | 5880 | 4.6 |
| Control | 5740 | 5210 | 0.9 |
| Example XXI | 5740 | 39860 | 6.9 |
| Control | 11800 | 23155 | 2.0 |
| Example XXI | 11800 | 157155 | 13.3 |
| Control | 21720 | 152345 | 7.0 |
| Example XXI | 21720 | 436070 | 20.1 |

EXAMPLE XXVIII (Dosage Response Analysis of the Derivative)

A stock of the medium described in Example XXVI containing approximately 18,000 log-phase HFN 7.1 hybridoma cells per milliliter was prepared, and 5 ml aliquots were placed into each of several T-25 tissue culture flasks (Corning). In this quadruplicate analysis, either saline or varying amounts of derivatives from Example XXI were added to some of these replicate flasks, as indicated in Table IV. The flasks were sealed and placed in a 37° C. incubator for four days. The resultant cell concentration was then determined with a Coulter Counter (TM) particle counter. The final amount of the derivative and the final cell density in the experimental cultures are also indicated in Table IV.

TABLE IV

| Sample | Amount of Derivative (μl) | Derivative (μg/ml) | Final Cell Density (Cells/ml) (Average + SE) |
|---|---|---|---|
| Control | — | — | 1.9 ± 0.2 × $10^5$ |
| Saline | 100 | — | 1.9 ± 0.2 × $10^5$ |
| Saline | 250 | — | 1.7 ± 0.1 × $10^5$ |
| Example XXI | 10 | 4 | 2.7 ± 0.1 × $10^5$ |
| Example XXI | 50 | 18 | 2.9 ± 0.1 × $10^5$ |
| Example XXI | 75 | 27 | 3.2 ± 0.1 × $10^5$ |
| Example XXI | 100 | 35 | 3.8 ± 0.4 × $10^5$ |
| Example XXI | 250 | 86 | 3.9 ± 0.3 × $10^5$ |

EXAMPLE XXIX (Growth Effects of 2-Mercaptoethanol in the Presence and Absence of the Derivative)

Mercaptoethanol is known to slightly enhance the growth of some cultured mammalian cells, and is included in the formulation of some culture media (55 μM in OPTI-MEM (TM) medium, GIBCO). Accordingly, the example is a comparison of the claimed invention with a previously known cell growth enhancer. In this example 5 mls of the medium described in Example XXVI containing approximately 22,000 HFN 7.1 hybridoma cells/ml were placed in each of four T-25 tissue culture flasks. The following additions were then made to the four flasks.

Flask #1: Control
Flask #2: 0.5 ml 570 μM 2-Mercaptoethanol
Flask #3: 0.1 ml of the derivative from Example XXI
Flask #4: Mercaptoethanol as in Flask #2 and 0.1 ml of Example XXI.

The flasks were then tightly capped and placed in the incubator (37° C.). After four days of growth the cell numbers were determined with a Coulter Counter (TM) particle counter and are recorded in Table V below.

TABLE V

| Flask | Derivatized Prepolymer (μg/ml) | 2-Mercaptoethanol (μM) | Cells/ml on day 4 |
|---|---|---|---|
| #1 | — | — | 1.5 × $10^5$ |
| #2 | — | 57 | 1.7 × $10^5$ |
| #3 | 35 | — | 4.5 × $10^5$ |
| #4 | 35 | 57 | 4.4 × $10^5$ |

As indicated, the derivatized prepolymer elicited significant growth stimulation, and little or no effects were observed from the addition of mercaptoethanol alone or in combination with the derivative. Therefore, the effects of the derivative cannot be due to the presence of 2-mercaptoethanol in the preparation.

EXAMPLE XXX (Growth Effects of the Components in the Derivatives)

The following experiment explores the possibility that one of the components of prepolymer and polymer derivatives is responsible for the growth enhancement.

Five mls of the medium described in Example XXVI containing 15,000 HFN 7.1 hybridoma cells/ml were added to each of many T-25 tissue culture flasks. The appropriate volume of each of the samples tested was added to the flasks in quadrupilcate. The test samples included 2 controls, ethyleneoxide based polyol (Pluracol V7), cystamine, the compound prepared according to Example XVI wherein the compound lacks a polyol derivative and claimed derivatives made according to Examples XXI and XXII. The flasks were tightly capped and placed in the incubator for four days (37° C.). The final cell number was determined with a Coulter Counter (TM) particle counter, and the cell number as a percentage of the control cell numbers is indicated in brackets [ ]. The results are illustrated in Table VI.

Additional test results from media containing the derivative prepared in Example XVA and a different polyol, e.g. BASF 1123, are included in Table VIA. See Example D in Experiments I and II.

TABLE VI

| Sample | Sample ($\mu$l) | Final Polyol* ($\mu$g/ml) | Final Cystamine* ($\mu$M) | Final ME* ($\mu$M) | Cells/ml (Average ± SE) [% of control] |
|---|---|---|---|---|---|
| CONTROLS: | | | | | |
| No additions | — | — | — | — | $2.3 \pm 0.3 \times 10^5$ |
| Saline | 100 | — | — | — | $2.0 \pm 0.1 \times 10^5$ |
| COMPONENTS: | | | | | |
| Polyether triol (Pluracol V7) | 100 | 200 | — | — | $2.1 \pm 0.2 \times 10^5$ [100] |
| Cystamine | 40 | — | 35 | — | $2.5 \pm 0.1 \times 10^5$ [125] |
| Example XVI (CA, IPDI and ME) | 40 | — | 35 | 56 | $1.6 \pm 0.3 \times 10^5$ [80] |
| Enhancers (Example #) | | | | | |
| XXI | 100 | 35 | 46 | 1 | $4.3 \pm 0.4 \times 10^5$ [215] |
| XXII | 50 | 35 | 46 | 28 | $5.1 \pm 0.2 \times 10^5$ [255] |

*Present as covalently bonded adduct in prepolymer
CA = cystamine
IPDI = isophorone diisocyanate
ME = mercaptoethanol

TABLE VIA
(Effect of Polyol on Cell Growth)

| | Components ($\mu$M) | | | |
|---|---|---|---|---|
| Sample | BASF 1123 Polyol | Cysteamine | 2-Mercapto-ethanol | Cell Number as % (Control A) (Day 4) |
| EXPERIMENT I (Example) | | | | |
| A (control) | 7 | — | 55 | 100 |
| B | — | 2.1 | 55 | 46 |
| C | 7 | 2.1 | 55 | 42 |
| D* | 7 | 14 | 55 | 193 |
| EXPERIMENT II (Example) | | | | |
| A (control) | 7 | — | 55 | 100 |
| B | — | 4.2 | 55 | 30 |
| C | 7 | 4.2 | 55 | 27 |
| D* | 7 | 14 | 55 | 195 |

*Derivative in experiment XVA

EXAMPLE XXXI

In Experiment A of Table VII, one gram of Pluracol V7 (BASF Wyandotte Corp.) and one gram of TPEG 10000 (Union Carbide) were each mixed with 9 grams of Hank's Buffered Saline (GIBCO) to produce 10% stock solutions of each. The solution and Hank's Buffered Saline (0.05 or 0.5 ml) were added to T-25 flasks containing 5 ml of 20,000 CLR1606 cells/ml of the medium described in Example XXVI. In Experiment B, a derivative made from Pluracol V7 was also tested. After five days the final cell density was determined using a Coulter Counter (TM) particle counter. The results are recorded in Table VII.

EXAMPLE XXXII

In Experiment C of Table VII, the polyol BASF 1123 and a derivative made from this polyol, e.g. Prepolymer E, high temperature, were tested as in Example XXXI for cell growth enhancement. The results from this addition are recorded in Table VII.

TABLE VII

| Experiment | Sample | Concentration of Polyol Component (mg/ml) | Cell Growth (% of control) |
|---|---|---|---|
| A | Control (HBS) | 0 | 100 |
| | Pluracol V7 | 10 | 96 |
| | Pluracol V7 | 1 | 97 |
| | TPEG 10000 | 10 | 95 |
| | TPEG 10000 | 1 | 95 |
| B | Control (HBS) | 0 | 100 |
| | Pluracol V7 | 0.2 | 91 |
| | EXAMPLE XXII | 0.04 | 187 |
| C | Control (HBS) | 0 | 100 |
| | BASF 1123 | 0.07 | 77 |
| | EXAMPLE XVA | 0.05 | 136 |

EXAMPLE XXXIII
(Effects of Cystamine Modified Prepolymers D and G)

In this example a monovalent prepolymer D (one isocyanate group per molecule) and divalent prepolymer G (two isocyanate groups per molecule) were used to prepare growth enhancement derivatives by modifying them with cystamine; see Examples XXIII and XVII.

Five mls of the medium described in Example XXVI containing 15,000 HFN 7.1 hybridoma cells/ml were added to each of many T-25 tissue culture flasks. One hundred microliters of saline and the derivative was added to the appropriate flasks. The stock solutions of the derivatives contained approximately 13 mg/ml polyol (present as a covalently bonded adduct in the derivative preparations). The flasks were tightly capped and placed in the incubator for four days (37° C.). The final cell number was determined with a Coulter Counter (TM) particle counter. This was a quadruplicate analysis, and the relative cell density (with respect to the saline control) observed after four days of growth is tabulated and recorded in Table VIII below.

TABLE VIII

| Sample | Relative Cell Density |
|---|---|
| Saline | 1.00 |
| Modified Prepolymer D (Ex. XXIII) | 1.55 ± 0.16 |
| Modified Prepolymer G (Ex. XVII) | 1.58 ± 0.24 |

Both of these preparations (when present at these concentrations) stimulate cell growth.

Derivatives Prepared with Other Sulfur Containing Primary Amines

EXAMPLE XXXIV (Antibody Production Stimulation by Cystamine Modified Prepolymer A and by Taurine Modified Prepolymer A)

The following demonstrates that cell growth enhancing derivatives can be prepared with other sulfur-containing primary amines in which the sulfur is present in another oxidation state. Furthermore, these preparations were made under conditions where no hydrogel was formed. Also it is demonstrated that no toxic materials were produced during the derivative formation, thus indicating that these materials were washed from the hydrogel during the hydration procedure. The results are tabulated in Sections A and B of Table IX below.

In this case the HFN 7.1 hybridoma cells (29,000/ml in Section A and 32,000 cells/ml in Section B, 5 ml/T-25 flask) were cultured in WRC 935 TM medium commercially available from Amicon Division of Grace Specialty Chemicals Co., W. R. Grace & Co.-Connecticut. Unless indicated otherwise, WRC 935 medium indicated in Sample 1 of Table X was used in the following examples.

In Section A of Table IX below, 0.25 ml of each of the derivative preparations, e.g. XXIV and XXV, and the indicated control solutions were added to duplicate flasks. In Section B, three different concentrations of the derivative produced in Example XXV were examined. The concentrations were varied to compare the effect of concentrations on both cell growth and antibody production. The test concentrations are indictaed in parentheses and are expressed as a percentage of the amount examined in Section A. The flasks were then tightly sealed and placed in the (37° C.) incubator for either five days (Section A) or three days (Section B). The final cell density was determined with a Coulter Counter (TM) particle counter, and the antibody concentration measured by ELISA. In Table IX the growth of the cells is expressed as relative increase in cell density (#cells final/#cells inoculated), and the antibody production is normalized to a per cell basis for comparative purposes.

TABLE IX

| Sample | # Cells Initial/ # Cells Final | Antibody Production (μg/million cells) (Average ± SE) |
|---|---|---|
| (A) FIVE DAYS GROWTH | | |
| Control, no additions | 16.0 | 20.5 ± 1.8 |
| Control, saline | 16.6 | 21.6 ± 2.8 |
| Control, saline + ME | 16.2 | 18.8 ± 0.2 |
| Control, average | 16.3 | 20.2 ± 2.0 |
| Ex. XXIV | 19.4 | 38.8 |
| Ex. XXV | 18.0 | 27.8 ± 1.4 |
| (B) THREE DAYS GROWTH | | |
| Control, no additions | 6.8 | 23.4 ± 2.8 |
| Ex. XXV (1.2%) | 7.7 | 28.4 ± 0.2 |
| Ex. XXV (12.4%) | 10.1 | 37.0 ± 1.7 |
| Ex. XXV (117.6%) | 11.3 | 27.8 |

ME = mercaptoethanol

EXAMPLE XXXV (Effect of Cysteamine Modified Prepolymer E, High Temperature)

HFN 7.1 murine hybridoma cells were seeded in roller bottles at 20,000 cells per ml in WRC 935 TM medium containing protein supplements indicated in Sample 1 of Table X. Additional proteins or cysteamine-derivatized prepolymer as indicated in Table X were added, and the cultures were incubated at 1.5 revolutions per minute at 37° C. Levels of anti-human fibronectin antibody were determined on Days 4 and 5 of continuous batch culture.

TABLE X

| Sample | Media Content | IgG (mg/l) | |
|---|---|---|---|
| | | DAY 4 | DAY 5 |
| 1 | WRC 935 Medium including commercial supplement insulin 5 μg/ml transferrin 5 μg/ml albumin 50 μg/ml | 27 | 80 |
| 2 | WRC 935 medium plus 2X proteins (Insulin, 10 μg/ml; transferrin, 10 μg/ml; albumin 100 μg/ml | 40 | 105 |
| 3 | WRC 935 media plus 20 μg of derivative prepared in Example XVA | 48 | 108 |
| 4 | WRC 935 media plus 2X proteins as in Sample 2 above and 20 μg of derivative prepared in Example XVA | 53 | 149 |

EXAMPLE XXXVI (Effects of Cystamine Modified Prepolymers B and Prepolymer E, High Temperature)

The derivatives produced according to Examples XIV (derivative from prepolymer B) and XVA (derivative of prepolymer E, high temperature) were added to WRC 935 TM media at 75 mg/l and 50 mg/l respectively. See Table XI below.

TABLE XI

| Addition | Initial Cell Number (×10⁴) | Final Cell Number (×10⁴) | IgG (μg/10⁶ cells) |
|---|---|---|---|
| None (WRC 935 | 2 | 52 | 79 |

TABLE XI-continued

| Addition | Initial Cell Number (×10⁴) | Final Cell Number (×10⁴) | IgG (μg/10⁶ cells) |
|---|---|---|---|
| medium) | | | |
| Example XVA (50 mg/l) | 2 | 100 | 107 |
| Example XIV (75 mg/l) | 2 | 100 | 98 |

TABLE XII (Effect of Polymer Derivatives on Cell Growth)
CELL NUMBER
(× 10⁴)

| Day | Control* | Medium Plus 59 mg/l Example XII | Medium Plus 67 mg/l Example XV |
|---|---|---|---|
| 0 | 2 | 2 | 2 |
| 1 | 4 | 5 | 5 |
| 2 | 5 | 8 | 7 |
| 3 | 11 | 19 | 15 |
| 4 | 36 | 55 | 44 |
| 5 | 63 | 120 | 130 |

| Day | Control* | Medium Plus 10 mg/l Example XXII | Medium Plus 50 mg/l Example XVA |
|---|---|---|---|
| 0 | 2 | 2 | 2 |
| 3 | 9 | 16 | 22 |
| 4 | 24 | 64 | 65 |
| 5 | 67 | 110 | 100 |

*Culture Medium - WRC 935 Medium plus protein supplements indicated in Sample 1 of Table X

ADDITIONAL MODIFIED PREPOLYMERS

EXAMPLE XXXVII (2,2'-Dithiodiethanoic Acid Modification of Prepolymer E, High Temp.)

A solution was prepared by dissolving 170.0 mg 2,2'-dithiodiethanoic acid in 20.0 ml acetonitrile. This solution was added to 4.4 gm Prepolymer E, high temp. and stirred until the prepolymer appeared to be dissolved. This calculates to be 1.0 mole equivalence of carboxylic group for the NCO groups on the prepolymer. Carbon-13 NMR spectrum of the sample after one week showed that only 5-10% of the NCO groups had reacted with the carboxylic group. At that point an equivalent amount of N-methyl imidazole was added to ionize all the carboxylic groups. Formation of gel occurred at room temperature in approximately 24 hours. The gel was shaken for 4 hours with 20.0 ml of acetonitrile, and excess of 2,2-dithiodiethanoic acid and N-methyl imidazole was poured off.

To the washed gel, 20.0 ml of 200 mM 2-mercaptoethanol solution in acetonitrile was added to reduce the disulfide bond of 2,2'-dithiodiethanoic acid in order to express -SH as the free functional group of the modified prepolymer. After 12 hours, the gel had completely dissolved. The compound was dialyzed against 55 mM 2-mercaptoethanol and filtered sterilized prior to use.

EXAMPLE XXXVIII (3,3'-dithiodipropionic Acid Modification of Prepolymer E, High Temp.)

A solution was prepared by suspendeing 200 mg 3,3'-dithiodipropionic acid in 5 mL acetonitrile followed by dropwise addition of 160 mg of N-methyl imidazole. This solution was added to a Prepolymer E (high temperature) solution in acetonitrile (4.4g Prepolymer E in 18 ml acetonitrile) and the solution shaken for 30 minutes. This calculates to be 1.0 mole equivalence of carboxylic groups to prepolymer NCO groups. Gel formation occurred at room temperature after approximately 24 hours. The gel was shaken for 4 hours with 20.0 ml of acetonitrile and then the excess 3,3'-dithiodipropionic acid and N-methyl imidazole was poured off.

To the washed gel, 20.0 ml of 200 mM 2-mercaptoethanol solution in acetonitrile was added to reduce the disulfide bond of 3,3'-dithiodipropionic acid. After 12 hours, the gel had completely dissolved. The compound was dialyzed against 55 mM 2-mercaptoethanol and filtered sterilized prior to use.

EXAMPLE XXXIX (Oxidized Glutathione Modification of Prepolymer E, Low Temp.)

Five fold excess glutathione -S-S-glutathione (oxidized) was added to prepolymer E, low temp. in order to ensure that all the isocyanates on the prepolymer were end capped. Specifically, glutathione (oxidized), 10.0 g (mole wt. 656.6), was dissolved in 234 ml of 25 mM sodium bicarbonate, pH 9.0. To this solution was slowly added 1.56 g prepolymer E (low temp.) dissolved in 15.6 g acetonitrile and the mixture was stirred. The solution was dialyzed against water to remove excess reactants.

EXAMPLE XL (Reduced Glutathione Modification of Prepolymer E, Low Temp.)

The derivative in Example XXXIX above was added to excess 2-mercaptoethanol to reduce the disulfide bond of glutathione. The resulting derivative was dialyzed against 55 mM mercaptoethanol and filtered sterilized prior to use.

EXAMPLE XLI (Cystine Modification of Prepolymer E, Low Temp.)

Five fold excess cystine was added to prepolymer E, low temp. in order to ensure that all the isocyanates on the prepolymer were end capped. Cystine, 14.68 was dissolved in 300 ml of 25 mM sodium bicarbonate, pH 9.0. To this solution was slowly added 20 g prepolymer E (low temp.) dissolved in 20 g acetonitrile and the mixture was stirred. The solution was dialyzed against water to remove excess reactants.

EXAMPLE XLII (Reduced Cystine Modification of Prepolymer E, Low Temp.)

The derivatives in Example XLI above was added to excess 2-mercaptoethanol to reduce the disulfide bond of cystine to cysteine. The resulting derivative was dialyzed against 55 mM mercaptoethanol and filtered sterilized prior to use.

TABLE XIII (Effects of Additional Modified Prepolymers on Cell Growth)

| Sample | Media Content | Cell Number (× 10⁵) | | | |
|---|---|---|---|---|---|
| | | Day 0 | Day 3 | Day 4 | Day 5 |
| 1 | Control* *HFN 7.1 cells in WRC 935 ᴛᴍ Medium | 0.2 | 0.9 | 3.3 | 6.8 |
| 2 | WRC 935 Media Plus 50 mg/l modified | 0.2 | 3.1 | 7.6 | 11.4 |

TABLE XIII-continued (Effects of Additional Modified Prepolymers on Cell Growth)

| Sample | Media Content | Cell Number (× 10⁵) | | | |
|---|---|---|---|---|---|
| | | Day 0 | Day 3 | Day 4 | Day 5 |
| | prepolymer in Example XXXVII (Prepolymer E, High Temp. modified by thioethanoic acid) | | | | |
| 3 | WRC 935 Media Plus 50 mg/l modified prepolymer in Example XXVIII (Prepolymer E, high temp. modified by thiopropionic acid) | 0.2 | 3.7 | 8.7 | 12.4 |
| 4 | Control in #1 | 0.2 | 1.9 | 4.5 | 9.8 |
| 5 | WRC 935 Media Plus 50 mg/l modified prepolymer in Example XVA (reduction product of Prepolymer E, High Temp. modified by Cystamine) | 0.2 | 3.0 | 7.1 | 15.0 |
| 6 | WRC 935 Media Plus 50 mg/l modified prepolymer in Example XL (reduction product of Prepolymer E, Low Temp. modified by Glutathione) | 0.2 | 2.2 | 6.0 | 13.9 |
| 7 | WRC 935 Media Plus 50 mg/l modified prepolymer in Example XLII (reduction product of Prepolymer E, High Temperature modified by cystine) | 0.2 | 3.0 | 9.7 | 16.2 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A modified hydrophilic polymer comprising oxyethylene-based diols or polyol units on which at least some of the hydroxy groups have been capped with polyisocyanate wherein the isocyanates of said polyisocyanates have been modified by an isocyanate (NCO) reactive functional group and wherein said modified polymer expresses a free functional group, said isocyanates being modified to the extent that said modified polymer effectively enhances mammalian cell growth and/or stimulates antibody production.

2. A modified polymer according to claim 1 wherein said NCO reactive functional group is a member of the group consisting of sulfhydryl, amino and carboxyl.

3. A modified polymer according to claim 1 wherein said free functional group is a member of the group consisting of amino, sulfhydryl and sulfonic acid.

4. A modified polymer according to claim 1 wherein said NCO reactive functional group is a sulfhydryl which is under conditions which form a thiolate anion and said polymer contains at least one thiourethane linkage and said free functional group of said modified polymer is amino.

5. A modified polymer according to claim 1 wherein said NCO reactive functional group is an amino and said modified polymer contains at least one urea linkage.

6. A modified polymer according to claim 5 wherein said polymer contains a disulfide bond and said free functional group is amino.

7. A modified polymer according to claim 1 wherein said free functional group is sulfhydryl and said modified polymer stimulates antibody production.

8. A modified polymer according to claim 1 wherein said NCO reactive functional group is carboxyl and said modified polymer contains at least one amide linkage and said free functional group is sulfhydryl.

9. A modified polymer according to claim 1 wherein said NCO reactive functional group is amino and said free functional group is sulfonic acid.

10. A modified polymer according to claim 1 wherein said free functional group is sulfonic acid and said modified polymer stimulates antibody production.

11. A cell growth enhancer and precursor to an antibody production stimulator comprising a dissolvable hydrophilic, biocompatible hydrogel wherein said hydrogel comprises a modified polymer containing disulfide bonds, said polymer being derived from oxyethylene-based diols or polyols in which at least some of the hydroxy groups have been capped with polyisocyanate and the isocyanates of said polyisocyanate have been modified by an isocyanate (NCO) reactive funetional group.

12. A cell growth enhancer and precursor according to claim 11 wherein up to 50% of the isocyanate groups of said polymer are modified by the NCO reactive functional group.

13. A cell growth enhancer and precursor according to claim 12 wherein about 20 to about 30% of the isocyanate groups of said polymer are modified by said NCO reactive functional group.

14. A cell growth enhancer and precursor according to claim 11 wherein said polyisocyanate is a member from the group consisting of aliphatic and cycloaliphatic polyisocyanates.

15. A cell growth enhancer and precursor according to claim 14 wherein said polyisocyanate is isophorone diisocyanate.

16. A cell growth enhancer and precursor according to claim 11 wherein said NCO reactive functional group is amino and said hydrogel contains at least one urea linkage.

17. A cell growth enhancer and precursor according to claim 11 wherein said modified polymer expresses a free amino.

18. A cell growth enhancer and precursor according to claim 11 wherein said NCO reactive group is a carboxyl and said hydrogel contains at least one amide linkage.

19. A cell growth enhancer and/or antibody production stimulator comprising a modified hydrophilic prepolymer wherein said prepolymer is an oxyethylene-based monofunctional alcohol, diol or polyol which at least some of the hydroxy groups have been capped with a polyisocyanate, wherein the isocyanates of said polyisocyanate have been modified by an isocyanate (NCO) reactive functional group to an extent that said prepolymer will not polymerize through said isocyanates, and wherein the modified prepolymer expresses a free functional group.

20. A cell growth enhancer according to claim 19 wherein at least 50% of said isocyanates have been modified by said NCO reactive functional group.

21. A cell growth enhancer according to claim 19 wherein substantially all of said isocyanates have been modified by said NCO reactive functional group.

22. A cell growth enhancer according to claim 19 wherein 100% of said isocyanates have been modified by said NCO reactive functional group.

23. A cell growth enhancer according to claim 19 wherein said NCO reactive functional group is a member of the group consisting of amino, sulfhydryl and carboxyl.

24. A cell growth enhancer according to claim 19 wherein said free functional group is a member of the group consisting of amino, sulfhydryl and sulfonic acid.

25. A cell growth enhancer according to claim 19 wherein said NCO reactive functional group and free functional group are aminos and said modified prepolymer contains a disulfide bond.

26. A cell growth enhancer according to claim 19 wherein said NCO reactive functional group is amino and said free functional group is sulfhydryl, wherein said cell growth enhancer stimulates antibody production.

27. A cell growth enhancer according to claim 19 wherein said NCO reactive functional group is a sulfhydryl under conditions which form a thiolate anion and said prepolymer contains at least one thiourethane linkage and said free functional group is amino.

28. A cell growth enhancer according to claim 19 wherein said NCO reactive functional group is carboxyl and said prepolymer contains at least one amide linkage and said free functional group is sulfhydryl.

29. A cell growth enhancer according to claim 19 wherein said NCO reactive functional group is amino and said free functional group is sulfonic acid wherein said cell growth enhancer stimulates antibody production.

30. A process for producing a cell growth enhancer and antibody production stimulator comprising reacting a modified prepolymer and water in a prepolymer-to-water ratio of about 1:1 to about 1:20, said modified prepolymer prepared by:
    (a) reacting diols or polyols with polyisocyanate at an isocyanate-to-hydroxyl ratio of about 1.8 to about 2.2 so that essentially all of the hydroxy groups of said diols or polyols are capped with polyisocyanate resulting in a polyisocyanate-endcapped prepolymer and
    (b) reacting said prepolymer with a modifying compound containing at least one disulfide bond and having at least one isocyanate (NCO) reactive functional group wherein said modifying compound is present in quantities sufficient to modify up to about 30% of the isocyanate groups of said polyisocyanate capped prepolymer,
    (c) reacting said modified prepolymer with water to form a polyurea-urethane polymer gel and
    (d) dissolving said polyurea-urethane polymer gel with a base catalyst or disulfide reducing agent so that said dissolution product expresses a sulfhydryl.

31. A process according to claim 30, wherein the reaction in (b) is carried out in an aqueous medium, thus resulting in simultaneous modification and polymerization.

32. A process according to claim 30 wherein said NCO reactive functional group of said modifying compound is amino.

33. A process according to claim 32 wherein said modifying compound is cystamine.

34. A process according to claim 30 wherein said NCO reactive functional group is carboxyl.

35. A cell growth enhancer and antibody production stimulator comprising the product of the processes as defined in any one of claims 30–34.

36. A process for producing a cell growth enhancer and/or antibody production stimulator comprising
    (a) reacting polyisocyanate-capped oxyethylene based monofunctional alcohol, diol or polyol prepolymer units with
    (b) a modifying compound having at least two functional groups wherein at least one functional group is an isocyanate (NCO) reactive functional group such that at least a portion of the isocyanate groups of said prepolymer are modified by the NCO reactive functional group and said modified prepolymer expresses a free functional group.

37. A process according to claim 36 wherein substantially all of said isocyanate groups are modified by said NCO reactive functional group.

38. A process according to claim 36 wherein 100% of said isocyanate groups are modified by said NCO reactive functional groups.

39. A process for producing a cell growth enhancer comprising
    (a) reacting polyisocyanate-capped oxyethylene based monofunctional alcohol, diol or polyol prepolymer units with a modifying compound having at least two functional groups wherein at least one functional group is an isocyanate (NCO) reactive functional group such that at least 50% of the isocyanate groups of said prepolymer are modified by the NCO reactive functional group and
    (b) polymerizing said modified prepolymer to form soluble polymeric units which express a free functional group and enhance mammalian cell growth.

40. A process according to claim 36 or 39 wherein said NCO reactive functional group and free functional group are aminos and said modifying compound contains a disulfide 41. A process according to claim 40 wherein said disulfide bond is reduced by a reducing agent so that said free functional group is sulfhydryl and said cell growth enhancer stimulates antibody production.

42. A process according to claim 41 wherein said disulfide bond is reduced by mercaptoethanol.

43. A process according to claim 41 wherein said modifying compound is cystamine.

44. A process according to claim 41 wherein said modifying compound is cystine.

45. A process according to claim 41, wherein said modifying compound is glutathione.

46. A process according to claims 36 or 39 wherein said NCO reactive group is sulfhydryl under conditions which form a thiolate anion and said free functional group is amino.

47. A process according to claim 46 wherein said modifying compound is cysteamine.

48. A process according to claim 46 wherein said modifying compound is cysteine.

49. A process according to claim 46 wherein said modifying compound is glutathione-SH.

50. A process according to claim 36 or 39 wherein said NCO reactive functional group is amino and said free functional group is sulfonic acid and said cell growth enhancer stimulates antibody production.

51. A process according to claim 50 wherein said modifying compound is taurine.

52. A process according to claim 36 or 39 wherein said NCO reactive functional group is carboxyl and said free functional group is sulfhydryl.

53. A process according to claim 52 wherein said modifying compound is thioethanoic acid.

54. A process according to claim 50 wherein said modifying compound is thiopropionic acid.

55. A cell growth enhancer comprising a member of the group consisting of the products of processes as defined in any one of claims 36, 39, 43, 47, 48, 49 and 51.

56. A cell growth enhancer and antibody production stimulator comprising a member of the group consisting of the products of processes as defined in claims 41, 42, 51, 52, 53 and 54.

57. A cell culture media with or without serum containing a cell growth enhancer according to claims 1, 19 or 55.

58. A cell culture media with or without serum containing a cell growth enhancer and antibody production stimulator according to claims 7, 26 or 56.

59. A method of enhancing cell growth by culturing said cells in a media defined in claim 57.

60. A method of enhancing cell growth and stimulating antibody production by culturing cells in a media defined in claim 58.

* * * * *

UNITED STATES PATENT AND TRADEMARK OFFICE
CERTIFICATE OF CORRECTION

PATENT NO. : 4,929,706

DATED : May 29, 1990

INVENTOR(S) : S. H. Heifetz et al.

It is certified that error appears in the above-identified patent and that said Letters Patent is hereby corrected as shown below:

Column 40, line 46, in claim 40, after "disulfide", insert --bond.--.

Signed and Sealed this

Twenty-first Day of April, 1992

Attest:

HARRY F. MANBECK, JR.

*Attesting Officer*  *Commissioner of Patents and Trademarks*